US010174068B2

(12) United States Patent
Cailly et al.

(10) Patent No.: US 10,174,068 B2
(45) Date of Patent: Jan. 8, 2019

(54) METHODS OF FUNCTIONALIZATION AND REAGENTS USED IN SUCH METHODS USING AN AZA-ISATOIC ANHYDRIDE OR A DERIVATIVE THEREOF, BIOLOGICAL MOLECULES THUS TREATED AND KITS

(71) Applicant: BIOMERIEUX, Marcy l'Etoile (FR)

(72) Inventors: Thomas Cailly, Caen (FR); Frédéric Fabis, Mathieu (FR); Ali Laayoun, La Frette (FR); Alain Laurent, Grenoble (FR); Sylvain Ursuegui, Caen (FR)

(73) Assignee: BIOMERIEUX, Marcy l'Etoile (FR)

( * ) Notice: Subject to any disclaimer, the term of this patent is extended or adjusted under 35 U.S.C. 154(b) by 607 days.

(21) Appl. No.: 14/416,996

(22) PCT Filed: Jul. 26, 2013

(86) PCT No.: PCT/EP2013/065854
§ 371 (c)(1),
(2) Date: Jan. 23, 2015

(87) PCT Pub. No.: WO2014/019966
PCT Pub. Date: Feb. 6, 2014

(65) Prior Publication Data
US 2015/0210732 A1 Jul. 30, 2015

(30) Foreign Application Priority Data
Aug. 2, 2012 (FR) ...................... 12 57526

(51) Int. Cl.
*C07H 21/02* (2006.01)
*C07D 405/02* (2006.01)
(Continued)

(52) U.S. Cl.
CPC ........... *C07H 21/02* (2013.01); *C07D 213/80* (2013.01); *C07D 405/02* (2013.01);
(Continued)

(58) Field of Classification Search
CPC .............................. C07H 21/02; C07D 405/02
(Continued)

(56) References Cited

U.S. PATENT DOCUMENTS

| 3,838,120 A | 9/1974 | Zalay et al. |
| 5,328,824 A | 7/1994 | Ward et al. |

(Continued)

FOREIGN PATENT DOCUMENTS

| DE | 3910151 A1 | 10/1990 |
| EP | 0063879 A2 | 11/1982 |

(Continued)

OTHER PUBLICATIONS

Weinstock Joseph and Boekelheide V. "Hofmann Degradation Studies on ß-Erythroidine. The Structure of Des-N-methyl-dihydro-ß-erythroidinol." vol. 75, pp. 2546-2550. 1953.
(Continued)

*Primary Examiner* — Jezia Riley
(74) *Attorney, Agent, or Firm* — Oliff PLC

(57) ABSTRACT

The present invention relates to a method of functionalization of at least one ribonucleic acid (RNA) molecule, contained in a liquid sample, which includes the following steps: a) providing at least: one binding molecule consisting of an aza-isatoic anhydride or a derivative thereof, one group of interest, and one linkage joining the binding molecule to the group of interest, b) reacting the anhydride function of the binding molecule with at least one hydroxyl group carried: in position 2' of the ribose of one of the RNA nucleotides, and/or in position(s) 2' and/or 3' of the ribose of the nucleotide at the terminal 3' end of the RNA, and obtaining an aza-anthranilate that joins, by means of the linkage, the RNA to the group of interest.

19 Claims, 5 Drawing Sheets

(51) Int. Cl.
    C07D 213/80    (2006.01)
    C07D 495/04    (2006.01)
    C07D 519/00    (2006.01)
    C07H 1/00      (2006.01)
    C12Q 1/6825    (2018.01)
(52) U.S. Cl.
    CPC ......... C07D 495/04 (2013.01); C07D 519/00
                (2013.01); C07H 1/00 (2013.01); C12Q
                                        1/6825 (2013.01)
(58) Field of Classification Search
    USPC ....................................................... 536/25.1
    See application file for complete search history.

(56) References Cited

U.S. PATENT DOCUMENTS

| | | | |
|---|---|---|---|
| 5,449,767 | A | 9/1995 | Ward et al. |
| 7,244,568 | B2 | 7/2007 | Goldsborough |
| 2004/0058941 | A1 | 3/2004 | Elliott et al. |
| 2004/0167123 | A1 | 8/2004 | Pratt et al. |
| 2004/0241192 | A1 | 12/2004 | Valiante |
| 2005/0106576 | A1 | 5/2005 | Akhavan-Tafti et al. |
| 2005/0106577 | A1 | 5/2005 | Akhavan-Tafti et al. |
| 2006/0241126 | A1 | 10/2006 | Elliott et al. |
| 2007/0148651 | A1 | 6/2007 | Michelsen et al. |
| 2009/0156605 | A1 | 6/2009 | Allen et al. |
| 2010/0035761 | A1 | 2/2010 | Weeks et al. |
| 2011/0224248 | A1 | 9/2011 | Allen et al. |
| 2012/0244182 | A1 | 9/2012 | Valiante |
| 2012/0270863 | A1 | 10/2012 | Williams et al. |
| 2013/0253179 | A1 | 9/2013 | Burr et al. |

FOREIGN PATENT DOCUMENTS

| | | |
|---|---|---|
| EP | 0097373 A2 | 1/1984 |
| EP | 0302175 A2 | 2/1989 |
| EP | 0329198 A2 | 8/1989 |
| EP | 0063879 B1 | 11/1989 |
| EP | 0567841 A2 | 11/1993 |
| EP | 0286898 B1 | 4/1998 |
| EP | 1510577 A1 | 3/2005 |
| EP | 1196631 B1 | 12/2006 |
| EP | 1771562 B1 | 5/2008 |
| EP | 1762618 B1 | 10/2008 |
| EP | 1479769 B1 | 11/2008 |
| EP | 1266385 B1 | 12/2008 |
| EP | 1476550 B1 | 5/2009 |
| EP | 1869179 B1 | 10/2009 |
| EP | 1448799 B1 | 11/2009 |
| EP | 1589105 B1 | 11/2009 |
| EP | 1383732 B1 | 2/2010 |
| EP | 1367137 B1 | 3/2010 |
| EP | 2185565 B1 | 8/2014 |
| FR | 2934595 A1 | 2/2010 |
| FR | 2968302 A1 | 6/2012 |
| WO | 93/16094 A2 | 8/1993 |
| WO | 02/30911 A1 | 4/2002 |
| WO | 02/090319 A1 | 11/2002 |
| WO | 2004/013155 A2 | 2/2004 |
| WO | 2004/064759 A2 | 8/2004 |
| WO | 2005/092910 A1 | 10/2005 |
| WO | 2007/145940 A2 | 12/2007 |
| WO | 2008/130600 A2 | 10/2008 |
| WO | 2009/040444 A1 | 4/2009 |
| WO | 2011/047432 A1 | 4/2011 |
| WO | 2012/076794 A1 | 6/2012 |

OTHER PUBLICATIONS

Wilkinson Kevin, Vasa Suzy, Deigan Katherine, Mortimer Stefanie, Giddings Morgan, and Weeks Kevin. "Influence of nucleotide identity of ribose 2'-hydroxyl reactivity in RNA." vol. 15, pp. 1314-1321, 2009.

Chamberlin Stacy and Weeks Kevin. "Mapping Local Nucleotide Flexibility by Selective Acylation of 2'-Amine Substituted RNA." Journal of American Chemical Society. vol. 122, pp. 216-224. American Chemical Society, 2000.

Huang Zhen and Szostak Jack. "A simple method for 3'-labeling of RNA." Nucleic Acids Research, vol. 24, No. 21 pp. 4360-4361. Oxford University Press, 1996.

Martin Georges and Keller Walter. "Tailing and 3'-end labeling of RNA with yeast poly(A) polymerase and various nucleotides." RNA, vol. 4 pp. 226-230. Cambridge University Press, 1998.

Huang Zhen and Szostak Jack. "Selective labeling and detection of specific RNAs in an RNA mixture." Analytical Biochemistry, vol. 315 pp. 129-133. 2003.

Ovodov S. Yu, and Alakhov Yu. B. "mRNA acetylated at 2'-OH-groups of ribose residues is functionally active in the cell-free translation system from wheat embryos." FEBS Letters vol. 270, No. 1,2 pp. 111-114. Elsevier Science Publishers, Sep. 1990.

Servillo Luigi, Balestrieri Ciro, Quagliuolo Lucio, Iorio Eugenio and Giovane Alfonso. "tRNA fluorescent labeling at 3' end inducing an aminoacyl-tRNA-like behavior." Eur. J. Biochem. vol. 213 pp. 583-589. 1993.

Deigan Katherine, Li Tian, Mathews David and Weeks Kevin. "Accurate SHAPE-directed RNA structure determination." PNAS vol. 160 No. 1 pp. 97-102, Jan. 6, 2009.

Mortimer Stefanie and Weeks Kevin. "A Fast-Acting Reagent for Accurate Analysis of RNA Secondary and Tertiary Structure by SHAPE Chemistry." JACS, vol. 129, pp. 4144-4145, 2007.

Mortimer Stefanie and Weeks Kevin. "Time-Resolved RNA Shape Chemistry." JACS vol. 130 pp. 16178-16180. 2008.

Gherghe Costin, Mortimer Stefanie, Krahn Joseph, Thompson Nancy, and Weeks Kevin. "Slow Conformational Dynamics at C2'-endo Nucleotides in RNA." JACS vol. 130 No. 28 pp. 8884-8885. 2008.

Wilkinson Kevin, Merino Edward and Weeks Kevin. "RNA SHAPE Chemistry Reveals Nonhierarchical Interactions Dominate Equilibrium Structural Transitions in tRNAAsp Transcripts." JACS vol. 127 pp. 4659-4667. 2005.

Coppola Gary, Fraser James, Hardtmann Goetz and Shapiro Michael. "The Chemistry of 3-Azaisotoic Anhydrides. Synthesis and Reactions of Polyaza Heterocycles." Journal of Heterocyclic Chemistry, vol. 22, Jan.-Feb. 1985 pp. 193-206.

Proudnikov Dmitri and Mirzabekov Andrei. "Chemical methods of DNA and RNA fluorescent labeling." Nucleic Acids Research vol. 24 No. 22 pp. 4535-4542, 1996.

Liang Ru-Qiang, Li Wei, Li Yang, Tan, Cui-yan, Li Jian-Xun, Jin You-Xin and Ruan Kang-Cheng. "An oligonucleotide microarray for microRNA expression analysis based on labeling RNA with quantum dot and nanogold probe." Nucleic Acids Research vol. 33 No. 2 e17, 2005.

Beuvink Iwan et al. "A novel microarray approach reveals new tissue-specific signatures of known and predicted mammalian microRNAs." Nucleic Acids Research, vol. 35 No. 7 e52, Feb. 27, 2007.

Wilkinson Kevin, Merino Edward and Weeks Kevin. "Selective 2'-hydroxyl acylation analyzed by primer extension (SHAPE): quantitative RNA structure analysis at single nucleotide resolution." Nature Protocols, vol. 1 No. 3 pp. 1610-1616, 2006.

Merino Edward, Wilkinson Kevin, Coughlan Jennifer and Weeks Kevin. "RNA Structure Analysis at Single Nucleotide Resolution by Selective 2'-Hydroxyl Acylation and Primer Extension (SHAPE)." JACS vol. 127 pp. 4223-4231, 2005.

Oct. 8, 2013 International Search Report issued in PCT Application No. PCT/EP2013/065854.

Oct. 8, 2013 Written Opinion of the International Searching Authority issued in PCT Application No. PCT/EP2013/065854.

Moorman A.R. and Abeles R.H. "A New Class of Serine Protease Inactivators Based on Isatoic Anhydride." JACS vol. 104 pp. 6785-6786, 1982.

Hiratsuka Toshiaki. "New Ribose-Modified Fluorescent Analogs of Adenine and Guanine Nucleotides Available as Substrates for Various Enzymes." Biochimica et Biophysica Acta vol. 742 pp. 496-508, 1983.

(56) References Cited

OTHER PUBLICATIONS

Vicens Quentin, Gooding Anne, Laederach Alain, and Cech Thomas. "Local RNA structural changes induced by crystallization are revealed by SHAPE." RNA vol. 13 pp. 536-548, 2007.

Winefordner J.D. Chemical Analysis: A Series of Monographs on Analytical Chemistry and its Applications vol. 162 p. 14.

Knorre D.G, Pustochilova N.M., Teplova N.M., and Shamovsky G.G. "The production of Transfer RNA Acetylated by 2'-Oxy Groups." vol. 75 pp. 1218-1224. Institute of Organic Chemistry, 1965.

Li Na, Wang Yuxuan, Pothukuchy Arti, Syrett Angel, Husain Naeem, Gopalakrisha Siddharth, Kosaraju Pradeepa, and Ellington Andrew. "Aptamers that Recognize Drug-Resistant HIV-1 Reverse Transcriptase." Nucleic Acids Research, vol. 36, No. 21, pp. 6739-6751. 2008.

McGinnis Jennifer, Dunkle Jack, Cate Jamie, Weeks Kevin. "The Mechanisms of RNA SHAPE Chemistry." Journal of the American Chemical Society. vol. 134, pp. 6617-6624. 2012.

METHODS OF FUNCTIONALIZATION AND REAGENTS USED IN SUCH METHODS USING AN AZA-ISATOIC ANHYDRIDE OR A DERIVATIVE THEREOF, BIOLOGICAL MOLECULES THUS TREATED AND KITS

The present invention relates to novel methods notably for functionalization, labelling, capture or separation of biological molecules, and more precisely of natural or synthetic ribonucleic acids (RNAs) or of synthetic DNA/RNA chimeric nucleic acids. Hereinafter, the term "functionalization" or the related terms (for example "functionalize") will be used and may also mean labelling with a detectable molecule, addition of an adduct allowing the capture, separation or inhibition of biological molecules. It also relates to biological molecules thus treated or labelled, as well as kits usable in the area of diagnostics, notably molecular diagnostics, using the detection and analysis of nucleic acids.

There are numerous methods in the prior art for functionalizing with groups of interest, nucleotides, oligonucleotides or nucleic acids, natural or produced by amplification techniques.

A first method consists of fixing the group of interest on the base, whether the latter is natural or modified. A second method proposes fixing the group of interest on the sugar, once again whether it is natural or modified. A third method relates to fixation of the group of interest on the phosphate.

The group of interest on the base has notably been used in the approach for labelling nucleic acids by incorporation of directly labelled nucleotides.

In general, functionalization at the level of the sugar is far more neutral than that performed on the phosphate or on the base, which affects the specificity and the sensitivity.

In fact a person skilled in the art, having to carry out a functionalization of a nucleotide or of a nucleotide analogue or of a nucleic acid, is inclined to perform this fixation on the base or on the sugar offering greater convenience and more alternatives. This is moreover what follows from studying a great many documents concerning labelling, notably such as EP-A-0,063,879, EP-A-0,097,373, EP-A-0,302,175, EP-A-0,329,198, EP-A-0,567,841, U.S. Pat. No. 5,449,767, U.S. Pat. No. 5,328,824, WO-A-93/16094 or DE-A-3,910,151 for the base or EP-B-0,063,879 or EP-B-0,286,898 for the sugar.

More specifically, functionalization on the sugar is often used in the case of nucleic acid probes prepared by chemical synthesis. There is, however, a need for groups of interest that are specific to the level of the position of fixation, and in particular that do not affect the hybridization properties of the bases involved in the formation of the double helix, via hydrogen bonds, and that are also specific to the RNAs, in order to functionalize, indifferently, ribonucleotides, oligoribonucleotides, RNA nucleic acids whether natural or prepared by transcription, nucleic acids comprising simultaneously at least one RNA part and at least one DNA part, by reverse transcription or by enzymatic amplification.

In the case of labelling and in order to make the targets detectable on DNA chips, it is necessary to fix a marker there beforehand. This is an important step, as this alone makes it possible to detect the presence of nucleic acids and establish a diagnosis. It is therefore important that the labelling technology should be extremely reproducible, robust and sensitive. This is directly correlated with the quality and the efficacy of the chemical reagent for labelling.

Moreover, in technologies for chemical functionalization, the group of interest must not affect the hybridization properties of the nucleic acids.

The applicant has, in the past, filed a certain number of patent applications relating to molecules comprising a diazo compound:
patent EP-B-1,383,732 filed on 3 May 2002, and granted on 17 Feb. 2010,
application EP05/739660.8 filed on 24 Mar. 2005,
application EP08/805961.3 filed on 9 Jun. 2008, and
application FR08/55190 filed on 29 Jul. 2008.

For information, the groups of interest based on a diazo function are not chemospecific to RNA nor regiospecific to a particular position. Therefore they functionalize DNA or RNA without differentiation. Moreover, the diazo function is poorly compatible with conjugation with certain cyanines, such as Cy5 for example.

Now, it is important to be able to be more specific in the mechanism of functionalization, for example for labelling:

A) In the case of DNA chips measuring the expression levels of mRNA, the RNA and it alone must be labelled. Now, in a complex biological sample, DNA and mRNA may be present and therefore labelled concomitantly. Using a marker that is not chemospecific to RNA, this may lead to an increase in background noise, during hybridization.

B) The marker, generally used in large excess, must be destroyed or removed before bringing the labelled nucleic acids in contact with the probes immobilized on the chip. In fact, there would otherwise be a risk of labelling the probes, which would lead to a result that is impossible to interpret. Having an RNA-specific marker would therefore make it possible to avoid this problem of labelling of the probes due to an excess of non-hydrolysed marker.

C) Owing to steric effects, it is less disturbing for hybridization between an oligonucleotide probe and a target consisting of nucleic acids to label on the ends of the target RNA strand (5' or 3') rather than internally. Now, the commercial labelling techniques do not allow such regiospecificity of labelling. To the best of our knowledge, only the chemical techniques of oxidation with periodate give this degree of specificity but they are severely affected by the complexity of the labelling protocol (more than three or four reagents and two or three purifications before we have labelled RNA); see, regarding this:

"An oligonucleotide microarray for microRNA expression analysis based on labeling RNA with quantum dot and nanogold probe" by Ru-Qiang Liang Nucleic Acids Research, 2005, Vol. 33, No. 2 e17 in Nucleic Acids Research, 1996, Vol. 24, No. 22 4535-4532, or "Chemical methods of DNA and RNA fluorescent Labeling" Nucleic Acids Research, 1996, Vol. 24, No. 22 4535-4532, by Dmitri Proudnikov.

In fact, regiospecific functionalization of the 3' ends of RNA can only be obtained using extremely specific enzymatic techniques. Such techniques are used for example by Affymetrix (Santa Clara, USA) or by Agilent Technologies (Santa Clara, USA) with specific labelling of RNAs at 3' with T4 RNA ligase and a substrate of the pCp-Marker type or by other enzymatic techniques described in certain references:

Huang Z. "Selective labeling and detection of specific RNAs in an RNA mixture" Analytical Biochemistry 2003 129-133, Martin G. "Tailing and 3'-end labeling of RNA with yeast poly(A) polymerase and various nucleotides". RNA 1998 22-230, or Huang Z. "A simple method for 3'-labeling of RNA" Nucleic Acids Research 1996 4360-4361.

The problem with the enzymatic techniques is their sensitivity to the type of substrate (size and sequence of the RNA to be labelled) and certainly their cost associated both with the substrate but especially with the enzyme.

Moreover, the recent development of the detection of microRNAs or miRNAs (short non-coding RNAs, intrinsic to eukaryotic cells) that may be markers of pathological conditions requires chemical labelling technologies that are practical and especially regiospecific for RNAs and notably for the 3' end for maximum limitation of the effects of steric hindrance, which are particularly pronounced on small duplexes. Moreover, these small oligomers are labelled very poorly by enzymatic techniques precisely because of their size, as described by F. Natt in the reference: Nucleic Acids Research, 2007, Vol. 35, No. 7 e52.

There is therefore great interest in having technologies for chemical functionalization of low cost, which as well as being specific for RNA would also be specific for the 3' end, completely independently of the size and sequence of the substrate to be labelled.

D) Although the diazo labelling technology is an excellent technique, the nature of the synthesis steps leading to these molecules is not compatible with the chemical nature of certain fluorophores (Cy5 for example, which is unstable in the presence of hydrazine). The diazo technology is therefore preferably used with biotin as the group of interest. Now, there is a real need for direct groups of interest bearing a fluorophore, in order to make additional steps unnecessary, such as the step of detecting the biotinylated compounds by a fluorescent streptavidin molecule. It is therefore important to have at our disposal versatile technology in which the group reacting with the nucleic acids (isatoic anhydride for example) is chemically compatible with conjugation with various groups such as Cy3 or Cy5 for example.

E) Finally, the chemo-selectivity of RNA versus DNA may also have applications in sample preparation, also called "sample prep", such as selection of RNAs without using a DNase, selective capture of RNA in a medium containing DNA, decontamination, selective inhibition of amplification, etc.

In 1982, Moorman (Moorman JACS 1982 104 6785-6786) published the use of isatoic anhydride for its selective reactivity with the serines of chymotrypsin, which leads to inactivation of the protein. This publication is one of the first to demonstrate the reactivity of isatoic anhydride on the hydroxyl groups of a biomolecule, in an aqueous medium. Curiously, however, whereas there was expected to be preferential reactivity with the amine functions present on the protein, the latter being more nucleophilic, it appeared that the alcohol functions react first.

In 1983, Hiratsuka (Hiratsuka BBA 1983 742 496-508) published one of the first articles on the reactivity of isatoic anhydride or methylated isatoic anhydride on free ribonucleosides (5' triphosphate or 5'-OH). This was for synthesizing fluorescent substrates of enzymes for studying the latter. In fact, isatoic anhydride, once open, becomes fluorescent. However, to avoid any confusion, we should draw a distinction between the intrinsic fluorescence of open isatoic anhydride, which becomes an anthranilate molecule (excitation: 335-350 nm and emission: 427-446 nm), and the fluorescence that is supplied by conjugation with a fluorophore. In fact we find numerous articles mentioning labelling of RNA with isatoic anhydride, but using the intrinsic fluorescence of the anthranilate for detecting it. Their conclusions are as follows:

isatoic anhydride does not react on the exocyclic amines of the bases, despite nucleophilicity usually described as being far greater than that of the 2'-OH, isatoic anhydride is not known to react on the 5'-OH, isatoic anhydride reacts preferentially (kinetically) on 2'-OH relative to 3'-OH (thermally favourable). However, owing to migration between the 2' and 3' positions of the acyl groups, a mixture of the order of 90% of ester at 3' is obtained.

In 1990, Ovodov (Ovodov, FEBS 1990 270 111-114), from research based on works of Khorana from 1963 (Stnark, Journal of the American Chemical Society 1963 75 2546 and Knorre Biokhimiya 1965 1218-1224), describes acylation of messenger RNAs in an aqueous medium with acetic anhydride (5% DMF, 1M sodium acetate, pH 7, 2 to 3 hours at room temperature) to protect the RNA against the action of the RNases. It describes a level of acylation of 70-75% sufficient for inhibiting the action of the RNases.

In 1993, Servillo (Servillo Eur. J. Biochem. 1993 583-589) published an article demonstrating specific "labelling" at 3', of transfer RNA, after incubation with isatoic anhydride (Molecular Probes, Eugene, USA) in aqueous medium and at a pH of 8.8 for 3 hours at room temperature. He demonstrates, by various techniques, absolutely regiospecific functionalization at 3'. By complete hydrolysis with RNase A and RNase T2, he shows the presence of a single fluorescent nucleoside. With inhibition of phosphodiesterase, he demonstrates full labelling in position 3', corresponding to regiospecific labelling without mentioning labelling at 5'.

In 2000, the first article was published in a continuing series by K. M. Weeks on the selective acylation of the hydroxyls at 2' of RNA. This series of articles is a counterbalance to Servillo's results in terms of the regiospecificity of the acylation since this time Weeks describes selective acylation of position 2'OH of RNA. It covers the literature on the SHAPE technique (Selective 2'-Hydroxyl Acylation and Primer Extension) and notably comprises the articles:

K. A. Wilkinson, S. M. Vasa, K. E. Deigan, S. A. Mortimer, M. C. Giddings and K. M. Weeks, Influence of nucleotide identity on ribose 2'-hydroxyl reactivity in RNA. RNA 15, 1314-1321 (2009).

K. E. Deigan, T. W. Li, D. H. Mathews and K. M. Weeks, Accurate SHAPE-directed RNA structure determination. Proc. Natl. Acad. Sci. USA 106, 97-102 (2009).

S. A. Mortimer and K. M. Weeks, Time-resolved RNA SHAPE chemistry. J. Am. Chem. Soc. 130, 16178-16180 (2008).

C. M. Gherghe, S. A. Mortimer, J. M. Krahn, N. L. Thompson and K. M. Weeks, Slow conformational dynamics at C2'-endo nucleotides in RNA. J. Am. Chem. Soc. 130, 8884-8885 (2008).

S. A. Mortimer and K. M. Weeks, A fast acting reagent for accurate analysis of RNA secondary and tertiary structure by SHAPE chemistry. J. Am. Chem. Soc. 129, 4144-4145 (2007).

K. A. Wilkinson, E. J. Merino and K. M. Weeks, Selective 2'-hydroxyl acylation analyzed by primer extension (SHAPE): quantitative RNA structure analysis at single nucleotide resolution. Nature Protocols 1, 1610-1616 (2006).

K. A. Wilkinson, E. J. Merino and K. M. Weeks, RNA SHAPE chemistry reveals non-hierarchical interactions dominate equilibrium structural transitions in tRNA$^{Asp}$ transcripts. J. Am. Chem. Soc. 127, 4659-4667 (2005).

E. J. Merino, K. A. Wilkinson, J. L. Coughlan and K. M. Weeks, RNA structure analysis at single nucleotide resolution by Selective 2'-Hydroxyl Acylation and Primer Extension (SHAPE). J. Am. Chem. Soc. 127, 4223-4231 (2005).

S. I. Chamberlin and K. M. Weeks, Mapping local nucleotide flexibility by selective acylation of 2'-amine substituted RNA. J. Am. Chem. Soc. 122, 216-224 (2000). and K. M. Weeks, The mechanism of RNA SHAPE chemistry, J. Am. Chem. Soc. 134, 6617-24 (2012).

The author uses derivatives of isatoic anhydride (N-methylated isatoic anhydride, isatoic anhydride, N-methylated nitro-isatoic anhydride, nitro-isatoic anhydride), which he reacts on transfer RNA or short model oligoribonucleotides (aqueous medium, pH 8, room temperature or 37° C., for some hours). Only the 2'-OH with little constraint, i.e. with little involvement in secondary or tertiary structures, are acylated, as they are more accessible and farther from a phosphate diester skeleton. They therefore become more reactive. Then this partially acylated RNA is submitted to in vitro transcription, which generates DNA fragments of varying length, elongation stopping whenever a bulky 2'-O-anthranilate, i.e. an open isatoic anhydride molecule that has become fixed on the 2'-OH of the sugar, is encountered. After sequencing or analysis of these fragments by capillary electrophoresis, it is possible to establish a map of the tertiary structure of the messenger RNAs thus submitted to this technique. This is the principle of the SHAPE technique (Selective 2'-Hydroxyl Acylation analysed by Primer Extension).

In 2008, an article by Li, "Aptamers that recognize drug-resistant HIV-1 reverse transcriptase" Na Li, Nucleic Acids Research, 2008, Vol. 36, No. 21 6739-6751, cites the works of Weeks for specifically labelling the 2'-OH internally, which would be the most accessible, and thus describing a structural map of the RNA in question.

In 2007, Thomas Cech (Cech T. R. RNA 2007 536-548) also used this technique for studying the structure of crystallized RNAs.

The prior art also comprises other patents concerning capture.

U.S. Pat. No. 7,244,568 relates to the selective acylation, more or less partial, of the 2'-OH of RNA with hydrophobic groups (butyryl or pentanoyl from the corresponding anhydrides). The RNA thus becomes sufficiently hydrophobic to be extracted selectively with an organic solvent, or to be selectively immobilized (for example on a reverse phase, silica, a membrane, etc.). It also describes a solid phase activated by an acid chloride or an anhydride that allows the RNA molecules to be immobilized selectively relative to the DNA molecules. This step may be carried out with immobilized isatoic anhydride or BCPB (benzyl chloride immobilized on polystyrene). Finally, a technique is also described for assay of the RNAs adsorbed on a solid phase: the 2'-OH of the immobilized RNAs are reacted with isatoic anhydride, and the intrinsic fluorescence generated makes it possible to analyse the immobilized RNA.

More detailed studies demonstrate that in the conditions advocated by this patent, the DNA is functionalized in the same way, because the anhydrides that are used are not chemospecific and attack both the exocyclic amines of the bases and the hydroxyl groups of the sugar.

Patent EP-B-1,196,631 proposes acylating agents compatible with regiospecific acylation of RNA in aqueous medium. These acylating agents must not supply excessive steric hindrance in order to maintain the hybridization properties of the RNA thus modified. It is mainly acylating agents for introducing an acetyl or formyl group that are used. The RNA thus partially modified then serves as matrix for a polymerization reaction, and it may also serve as probe in a Northern blot reaction. The idea is to maintain the hybridization properties (the modified RNA remains the substrate of an elongation reaction), while destroying the secondary structures by the presence of the group at 2' and by making the RNA thus modified resistant to nucleases. Moreover, example 22 indicates that fluorescent labelling of RNA is envisaged, but only by addition of methylated isatoic anhydride, therefore it is a question of intrinsic fluorescence.

Patent EP-B-1,196,631 proposes a polynucleotide comprising mRNA, rRNA or viral RNA, for which more than 25% of the riboses are modified covalently at the level of the 2'-OH positions. Moreover, it relates to a method for producing double-stranded oligonucleotides and polynucleotides from a starting nucleic acid strand, starting from a plurality of mononucleotides (UTP, dTTP and/or dUTP, ATP and/or dATP, GTP and/or dGTP, and CTP and/or dCTP), in the presence of polymerase and optionally of primers allowing formation of a strand of nucleic acid complementary to the starting nucleic acid.

Patent application WO-A-2004/013155 describes chemical modification of RNA in a mixture of the type of faeces, blood, etc., in order to differentiate the DNA from the RNA. The reagent capable of performing this differentiation is acetic anhydride. Then the ester function is hydrolysed in order to regenerate the biologically active RNA. For this, this application proposes protecting the use of organic bases that are "only slightly" aggressive towards RNA (lysine, diamines etc.), in combination with a deprotection protocol.

It is noted from all these documents that only the intrinsic fluorescence of isatoic anhydride once opened is used. Moreover, the use of this molecule and of its derivatives for other applications, as is proposed by the present invention, is not described.

Regarding the fluorescence of isatoic anhydride, there is little advantage in only having the fluorescence of isatoic anhydride for being able to detect RNAs. Thus, this fluorescence is weak compared to other fluorescent compounds and is not necessarily compatible with the wavelength of the lasers currently used in devices for automatic detection. Moreover, with the intrinsic fluorescence of open isatoic anhydride, the applications are limited to monoplex detection, and not multiplex as is more and more often the case in molecular biology. For example, labelling for applications in the field of DNA chips is not possible with these patents as the user will not be able to differentiate detection of a first type of nucleic acids from that of a second type of nucleic acids, both labelled with isatoic anhydride.

In the prior art, all told there are four different uses of isatoic anhydride. Firstly, it is a matter of exploiting the intrinsic fluorescence properties of esters of anthranilic acid for studying the mechanism of certain enzymes. Secondly, the use of the acylating properties of isatoic anhydride for regioselectively inhibiting the polymerization of nucleic acids; it is therefore only a matter of introducing a bulky substituent at 2' in conditions that are as mild as possible, in a more or less controlled manner. Thirdly, the prior art uses isatoic anhydride for preventing their degradation during an extraction step. Finally, fourthly, it is a matter of extracting the acylated RNA selectively relative to the non-acylated DNA. There is then an idea of reversibility of the ester function so as to regenerate a free 2'OH function and therefore a functional RNA.

The idea of conjugating the isatoic anhydride molecule to biotin or to a Cy3 for applications in the labelling of mRNAs for hybridization on at least two different spots or on a DNA chip therefore is not obvious as conjugation with a group of interest may lead to a change in acylating properties and even in the stability of isatoic anhydride, properties that are difficult to predict. In particular, conjugation of isatoic anhydride to the group of interest must be done by means of atoms and bonds that may lead to very marked destabilization of the structure, very great difficulty in synthesis, poor solubility in water, loss of the physicochemical properties of the group of interest through attenuation of the fluorescence, very poor reactivity with respect to RNA, very great instability of the duplexes formed between the labelled RNA and the DNA (probes for capture notably by excessive steric hindrance or because the functionalized RNAs/DNA hybrids are no longer substrates of polymerase).

The inventors moreover understood the advantage of functionalization of RNAs with isatoic anhydride compounds in order to allow their capture by recognition molecules whether or not carried by a solid support.

Moreover, they proposed a previous invention, WO-A-2012/076794, consisting of using isatoic anhydride not for its intrinsic fluorescence but for its capacity to bind specifically to RNA and allow binding with a group of interest, as defined later.

As stated above, one of the most widely used techniques for extraction of nucleic acids is a technique of adsorption on silica in the presence of chaotropic salts (so-called BOOM technology), which despite its efficacy and its great capacity for being automated, has the drawback of being generic and having little specificity for RNA, except by using elution buffers of complex formulation whose composition remains empirical.

Briefly, the technology is based on the particular affinity that develops between nucleic acids, silica and cations that would form the bond between the phosphate groups and the silanol residues present on the surface of the silica as is described in "Sample Preparation Techniques in Analytical Chemistry. Vol 162 Edited by S. Mitra Wiley-Interscience 2003".

A great many variants of BOOM technology have been protected for improving the extraction yield, and avoiding co-purification of amplification inhibitors.

In this connection, we may cite some patents describing improvements in BOOM chemistry.

Patent EP-B-1,367,137 describes improvement of BOOM technology using magnetic silica particles for extraction of nucleic acids, allowing much easier automation.

Patent EP-B-1,476,550 presents a method for purifying nucleic acids using a solid phase modified with thioethers and eluents consisting of lyotropic salts.

Patent EP-B-1,266,385 proposes ferromagnetic or ferrimagnetic silica particles for purification of nucleic acids.

Patent EP-B-1,762,618 discloses a solution for extracting nucleic acids from blood, consisting of 15 to 35% of guanidine and a detergent.

Patent EP-B-1,771,562 describes a new method for extraction of nucleic acids based on silica in the presence of organic aids.

Finally, patent EP-B-1,589,105 proposes extraction of nucleic acids at acid pH on magnetic particles not covered with silica.

However, although these techniques, based on non-covalent interactions between nucleic acids and a solid support, have until now mainly been used in the automatic systems used for extraction of nucleic acids, none allows specific discrimination of RNA from DNA. There is therefore a need to develop selective techniques.

Slightly more selective techniques for extracting nucleic acids by non-covalent interaction with a solid support have also been proposed. There are few documents expressly describing automated selective extraction, from a complex biological mixture, either only of RNA or only of DNA.

However, patent EP-B-1,448,799 presents more or less selective purification of nucleic acids on silica at alkaline pH in the presence of various anions.

Patent application EP-A-1,510,577 tries to protect the use of a mixture of chaotropic salts and hydrophilic additives for optimizing the separation of DNA relative to RNA.

Patent EP-B-1,479,769 describes and claims selective separation between RNA and DNA. This is based on changes in temperature, ionic strength and chemical composition of certain buffered solutions.

Patent EP-B-1,869,179 proposes the use of ligands specific for RNA or DNA for specific extraction of RNA relative to DNA.

Patent application US-A-2007/0148651 presents the specific extraction of RNA, from a mixture of DNA and RNA, by adsorption of the RNA on particles of magnetite in the presence of phosphate anions.

Patent application WO-A-2009/040444 describes selective precipitation of genomic DNA on chitosan-coated magnetite particles, from a DNA/RNA mixture. The RNA is then recovered from the supernatant by precipitation with alcohol.

Finally, we may mention patents US-A-2005/0106576 and US-A-2005/0106577 which protect: a nucleic acid binding portion (NABP), joined to a solid support by a cleavable linker. The NABP is a charged molecule having affinity for nucleic acids but no selectivity for RNA relative to DNA. Moreover, the NABP is carried on a solid support with all the drawbacks that this entails compared to our invention, such as non-specific adsorption, steric hindrance, etc.

It should be noted that all these techniques are also based on non-covalent interaction between the nucleic acids (RNA or DNA) and a solid phase, in the presence of various additives, which will modulate the adsorption thereof more or less selectively. The interactions involved in adsorption of the nucleic acids are of a weak nature (electrostatic, ionic, hydrophobic, hydrogen bonds, etc.) in comparison with a covalent bond.

It can therefore be seen that despite the attempts at improvement, no technique is really satisfactory, allowing absolute selectivity between RNA and DNA. There is therefore a real need to propose new innovative techniques.

Moreover, techniques for selective extraction of RNA versus DNA have been proposed. The only techniques for extracting RNA relatively selectively with a minimum of contamination with DNA are based on:
  chemical techniques such as extraction with phenol/chloroform (Trizol®), which although being effective, require the use of organic solvents and therefore have drawbacks in terms of toxicity, difficult automation, etc.,
  enzymatic techniques with addition of a DNase or RNase, but with the drawback of cost and the need for denaturation of these enzymes after their action,
  physicochemical techniques such as differential centrifugation on a caesium chloride salt gradient, which are extremely complex to automate and are based on the relative density of the biomolecules,
  techniques for specific capture using magnetic particles coated with poly-dT oligonucleotides for specifically recognizing the polyA sequences of messenger RNAs with the drawback that only the mRNAs are captured without the ribosomal RNAs, pRNAs and other "small" RNAs being recognized.

The corresponding patent application, WO-A-2012/076794, is incorporated here by reference. In this application, the applicant made a start to solving the problems of separation between RNA and DNA from a complex medium. It was proposed to discriminate RNA from DNA on the basis of their chemical composition. In fact the only difference between RNA and DNA is the presence of a hydroxyl group at 2' of the ribose. The objective was therefore to make use of this function for specifically coupling a binding molecule to it (a derivative of isatoic anhydride) equipped with a group of interest allowing molecular sorting to be performed between the two macromolecules, based on the specific recognition of the group of interest. The reactive binding molecule had to be able to react in mild conditions (65° C., for less than 1 hour, in aqueous medium).

By an appropriate choice of the groups of interest supplied on the RNA, for example certain groups having particular affinity for a solid phase, it is therefore possible to extract the RNA specifically from a complex medium.

After specific functionalization of the RNA, the latter can be immobilized on the solid phase whereas the purified DNA was eluted (but may be recovered in order to be amplified specifically). The RNA captured, free from DNA, may then be separated from its group of interest directly on the solid phase so that in its turn it can be specifically eluted and amplified.

This method therefore makes it possible to sort and separate RNA from DNA with very high selectivity, and consists of:
1—forming a covalent bond between the RNA and a binding molecule (derivative of isatoic anhydride) bearing a group of interest;
2—sorting the nucleic acid thus functionalized, by the group of interest, relative to that which has not been functionalized;
3—cleaving the bond between the RNA and the group of interest in order to release a biologically active RNA (anthranilate or bare), completely free from DNA. However, although the applicant demonstrated perfectly the reality of sorting RNA versus DNA, notably in example 14, there is still a desire to improve the efficacy of this protocol, essentially by designing a new family of the molecules based on aza-isatoic compounds that are more able to respond to these problems.

Thus, the present invention makes it possible to:
increase the reactivity of isatoic anhydride even more, so as to:
be able to functionalize at room temperature, and not at 65° C., so as to facilitate integration of this method in an automatic diagnostic system usable industrially,
minimize the consumption of aza-isatoic anhydride acylating reagent with a view to industrial application of this method (lowering the cost of reagent),
facilitate removal of the surplus reagent to improve integration of this protocol in a diagnostic platform,
increase enrichment with RNA relative to DNA even more.
increase the solubility in aqueous medium even more, always with the aim of facilitating removal of the surplus reagent and increasing its reactivity,
have, after reaction of the binding molecule and cleavage of the linkage, "bare" RNA, without aza-anthranilate groups (with the aim of avoiding any inhibition due to the aza-anthranilate),
apply the concept to other uses, such as:
endowing RNA with absolute resistance to nucleases by uncontrolled functionalization of the RNA,
inhibition of selective amplification of the RNA in an RNA/DNA mixture,
labelling of ribonucleic acids for a DNA chip application or others.

In the context of this patent application, we supply a novel solution for the sorting of RNA versus other molecules by means of a new molecule that is:
more reactive and therefore more effective as it is able to functionalize RNA at room temperature,
more economical as it requires a lower concentration for the same effect and accordingly is easier to remove,
more soluble, because the introduction of a pyridinyl group increases the solubility in an aqueous medium,
more selective and therefore more able to solve the problem of selective extraction,
optionally endowed with an additional functionality with a substituted methyl disulphide linkage which makes it possible to regenerate a bare RNA by cleavage, which avoids any problem of inhibition of subsequent amplification,
applicable to other uses.

By definition, a group of interest is a molecule which:
is a reactive molecule or a reactive group capable of reacting with another reactive molecule or another reactive group in certain conditions (example of a nucleophile and an electrophile, an alkyne with an azide, a maleimide with a thiol, a diene with an alkene, etc.), and/or
possesses intrinsic fluorescence that is different from that of the open isatoic anhydride (anthranilic ester), and/or
is a ligand that may be recognized by a recognition molecule or a surface, or a particle, etc., to form a complex that is stable and optionally reversible, of the biotin/streptavidin type, hydrophobic or hydrophilic molecule/hydrophobic or hydrophilic support, antigen/antibody, saccharide or polysaccharide/lectin, etc., and/or
is a marker molecule for an indirect reaction consisting of a ligand/receptor pair of the type:
biotin/streptavidin,
hapten/antibody,
antigen/antibody,
peptide/antibody,
saccharide or polysaccharide/lectin,
electrophilic molecule/nucleophilic molecule,
polynucleotide/complementary of the polynucleotide,
hydrophobic ligand/hydrophobic solid phase, or
ligand/coordination metal.

Binding molecule means an aza-isatoic anhydride or derivatives thereof. Note that when the aza-isatoic anhydride is open after reaction with a nucleophile, it then has the name aza-anthranilate.

Aza-isatoic anhydride derivatives means any organic compounds comprising a part corresponding to the aza-isatoic anhydride and bearing, on the aromatic part or on the heterocyclic part of the latter, at least one radical, such as a chemical group or organic group.

"Functionalization of at least one ribonucleic acid molecule" means the action of grafting a group of interest—by covalent or non-covalent bond—on said ribonucleic acid molecule. Depending on the type of group of interest grafted (marker, labelling precursor, group allowing capture by at least one capturing means, separation or inhibition of biological molecules etc.), the term "functionalization" or the related terms ("functionalize" for example) denote labelling—direct or indirect—of said ribonucleic acid molecule with a detectable molecule, addition of a group on said ribonucleic acid molecule allowing capture, separation or inhibition of the latter etc.

Linkage defines a spacer of organic nature, such as a simple covalent bond, allowing the binding molecule and the group of interest to be joined together. It may comprise a function that is cleavable by a physicochemical, photochemical, enzymatic, chemical, thermal means, etc.

Recognition or capturing means or molecule defines a molecule whether or not immobilized on a solid support having a strong affinity for the group of interest.

The definition of an RNA is a natural or synthetic polymer consisting of at least two successive ribonucleotide units, modified or not.

The term DNA is defined as a natural or synthetic polymer consisting of at least two successive deoxyribonucleotide units, modified or not.

It is also possible to use chimeric single strands consisting of at least one DNA segment and at least one RNA segment.

Inhibition means the inability of RNA, excessively functionalized with a derivative of isatoic anhydride, to be amplified by technology for amplification of genetic material (NASBA, PCR, etc.).

By definition, the word sugar is a ribose or deoxyribose compound.

Liquid sample means a homogeneous or heterogeneous aqueous solution in which the nucleic acids are completely soluble. The solution is said to be heterogeneous for example when it contains a solid support optionally with RNAs fixed on its surface.

The pyridinyl group is selected on the basis of the fact that in addition to solubility, its ability to attract electrons means that it increases the reactivity of the carbonyl function making it more capable of nucleophilic attack on the hydroxyl groups of the RNA.

The choice by the applicant of the position for substitution of the pyridinyl nucleus in position 6, 7 or 8 may also have an effect on the stability of the final molecule. Although for a person skilled in the art it is technically easier to substitute position 6 in the case of the BiotPEG4SS Pyr IA Me molecule (14), it is also possible to employ technical solutions for substituting positions 7 or 8.

In the case of introduction of two linkages, optionally bound to a group of interest, the difficulty of synthesis is further increased because a linkage allowing self-immolation of the anthranilate must necessarily be incorporated in position 5 (cf. formula (2) below and FIG. 2). Aza-isatoic molecules substituted twice with linkages have never been described for applications of sorting of biomolecules.

The present invention relates to a method of functionalization of at least one ribonucleic acid (RNA) molecule, contained in a liquid sample, which comprises the following steps:
a) providing at least:
one binding molecule consisting of an aza-isatoic anhydride or a derivative thereof,
one group of interest, and
one linkage joining the binding molecule to the group of interest,
b) reacting the anhydride function of the binding molecule with at least one hydroxyl group carried:
in position 2' of the ribose of one of the RNA nucleotides, and/or
in position(s) 2' and/or 3' of the ribose of the nucleotide at the terminal 3' end of the RNA, and
c) obtaining an aza-anthranilate that joins, by means of the linkage, the RNA to the group of interest.

The present invention also relates to a method of labelling at least one ribonucleic acid (RNA) molecule, contained in a liquid sample, which comprises the following steps:
a) providing at least:
one binding molecule consisting of an aza-isatoic anhydride or a derivative thereof, having an intrinsic fluorescence,
one group of interest, having an intrinsic fluorescence signal, different from the signal emitted by the binding molecule, or not having an intrinsic fluorescence signal, and
one linkage joining the binding molecule to the group of interest,
b) reacting the anhydride function of the binding molecule with at least one hydroxyl group carried:
in position 2' of the ribose of one of the RNA nucleotides, and/or
in positions 2' and/or 3' of the ribose of the terminal nucleotide in position 3' of the RNA, and
obtaining an aza-anthranilate that joins, by means of the linkage, the RNA to the group of interest.

The present invention also relates to a method for capturing or separating at least one ribonucleic acid (RNA) molecule, which comprises the following steps:
a) providing at least:
one binding molecule consisting of an aza-isatoic anhydride or a derivative thereof,
one group of interest consisting of a ligand complementary to an anti-ligand, and
one linkage joining the binding molecule to the group of interest,
b) reacting the anhydride function of the binding molecule with at least one hydroxyl group carried:
in position 2' of the ribose of one of the RNA nucleotides, and/or
in positions 2' and/or 3' of the ribose of the terminal nucleotide in position 3' of the RNA, and
c) obtaining an aza-anthranilate, joining by means of the linkage, the RNA to the group of interest,
d) capturing or separating the RNA via a reaction between a ligand and an anti-ligand.

In the context of the method for capture or separation, there may be an additional step consisting of:
e) reserving or discarding the RNA molecules thus captured or separated and using the rest of the DNA-enriched sample.

In all instances of the aforementioned methods, and according to a first embodiment, the linkage is associated with the binding molecule before said linkage is associated with the group of interest.

In all instances of the aforementioned methods, and according to a second embodiment, the linkage is associated with the binding molecule after said linkage is associated with the group of interest.

Regardless of the embodiment, the binding molecule is associated beforehand with the RNA.

The present invention always relates to a method of selective capture of at least one molecule of RNA using at least one binding molecule, one group of interest, consisting of a ligand complementary to an anti-ligand, and one linkage joining the binding molecule to the group of interest, the binding molecule consisting of an aza-isatoic anhydride or a derivative thereof, which is attached by a covalent bond at the level of a hydroxyl group carried:
in position 2' of the ribose of one of the RNA nucleotides, and/or in positions 2' and 3' of the ribose of the terminal nucleotide in position 3' of the RNA, and/or in position 3' of the ribose of said terminal nucleotide in position 3' of the RNA.

The present invention finally relates to a method of separating RNA molecules relative to other biological constituents, notably DNA molecules, consisting of:

applying the aforementioned method of capture to a biological sample containing undifferentiated nucleic acids (RNA and DNA), the groups of interest being associated with at least one solid support that can easily be separated from the rest of the biological sample, and separating the binding molecules bearing the RNA molecules from the rest of the biological sample.

The present invention also proposes a functionalizing reagent, of formula (1):

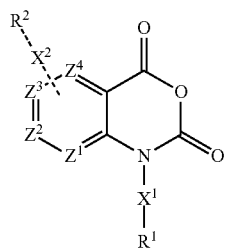

in which:

$R^1$ and $R^2$ represent, independently of one another, H or a group of interest, knowing that at least one of the radicals $R^1$ and $R^2$ is represented by a group of interest, and the group of interest may be:
a. a marker or a labelling precursor, or
b. a ligand that can be recognized by a recognition molecule or a surface, or a particle, etc., in order to form a stable complex, $X^1$ and $X^2$ each represent, independently of one another, a linkage that joins the group of interest to the binding molecule, just one of the radicals $Z^1$, $Z^2$, $Z^3$ and $Z^4$ consists of a nitrogen atom (N), and the other radicals consist of a carbon atom (C).

More precisely, the invention proposes a functionalizing reagent, of formula (2):

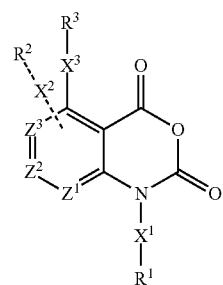

in which:

$R^1$, $R^2$ and $R^3$ represent, independently of one another, H or a group of interest, knowing that at least one of the radicals $R^4$, $R^2$ and $R^3$ is represented by a group of interest, and the group of interest may be:
a. a marker or a labelling precursor, or
b. a ligand that can be recognized by a recognition molecule or a surface, or a particle, etc., in order to form a stable complex, $X^1$, $X^2$ and $X^3$ each represent, independently of one another, linkages that join the group of interest to the binding molecule, just one of the radicals $Z^1$, $Z^2$ and $Z^3$ consists of a nitrogen atom (N), and the other radicals consist of a carbon atom (C).

The assembly consisting of the functionalizing reagents of formula (1) and those of formula (2) may also be represented by the following formula (I):

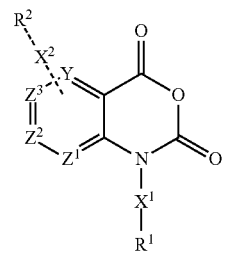

in which:

Y represents $Z^4$ or the group $C-X^3-R^3$, $R^1$, $R^2$ and $R^3$ (when $Y=C-X^3-R^3$) represent, independently of one another, H or a group of interest, knowing that at least one of the radicals $R^1$, $R^2$ and $R^3$ (when $Y=C-X^3-R^3$) represents a group of interest, and the group of interest is selected from:
c. a marker or a labelling precursor, or
d. a ligand that can be recognized by a recognition molecule or a surface, or a particle, etc., in order to form a stable complex, $X^1$, $X^2$ and $X^3$ (when $Y=C-X^3-R^3$) each represent, independently of one another, linkages that join the group of interest to the binding molecule, just one of the radicals $Z^1$, $Z^2$, $Z^3$ and $Z^4$ (when $Y=Z^4$) consists of a nitrogen atom (N), and the other radicals consist of a carbon atom (C).

Whatever reagent is used, if the latter is used for capture or separation, the capturing or separating means consists of a solid support, such as particles of polymer or of silica, magnetic or non-magnetic, or a filter or else the inside wall of a container.

Whatever reagent is used, if the latter is used for functionalization, the linkage X is an organic spacer allowing the binding molecule and the group of interest to be joined together, such as a simple covalent bond between the binding molecule and the group of interest or a single carbon atom, optionally substituted, a chain of at least two carbon atoms, optionally containing aromatic structures and/or heteroatoms (oxygen, sulphur, nitrogen, etc.).

According to this last embodiment of the functionalizing reagent, linkage X comprises a function or a bond capable of being cleaved by a physicochemical, photochemical, thermal, enzymatic and/or chemical means allowing separation of the binding molecule relative to RNA in particular conditions of light, of temperature, or enzymatic or chemical conditions.

The invention also has a biological molecule of functionalized RNA obtainable by one of the methods mentioned above.

The invention also proposes to cover a kit for detecting a target RNA molecule comprising a reagent, as described above.

Finally, regardless of the method, the invention relates to a method of functionalization, which comprises the following additional step between steps a) and b) consisting of hydrolysing the terminal monophosphate group in position 3' of each RNA strand to be functionalized.

In one embodiment, a linkage, whether or not bound to a group of interest, replaces the pyridinyl group. Moreover, the cleavable function is designed and is positioned in such a way that after cleavage it can form a cyclic heterocycle with 5 to ring members with the carbonyl function of the aza-anthranilate RNA and thus release a bare RNA, with its 2'-OH free (2), usable in any method of amplification, detection or protection of RNA and where necessary absolutely avoiding any potential inhibition that would be due to the aza-anthranilate.

This last-mentioned embodiment is preferably based on the formation of an aza-thiolactone, forming spontaneously during cleavage of the cleavable disulphide (—SS—) function of the linkage carried at position 5. Such self-immolating systems have never been described in the aza-isatoic series with the aim of releasing an RNA.

This last-mentioned embodiment makes it possible moreover to avoid the release of by-products during hydrolysis with DTT, the thiolactone remaining on the support. It is also possible to conceive similar systems with a cleavable function of the type —OR, —NR allowing, after removal of the group R, the release of an alcohol or amine function respectively, permitting cyclization with the carbonyl function of the RNA-anthranilate also for liberating a "bare" RNA.

The invention will be better understood from the detailed description presented below, referring to the appended figures, namely:

Figure 3:
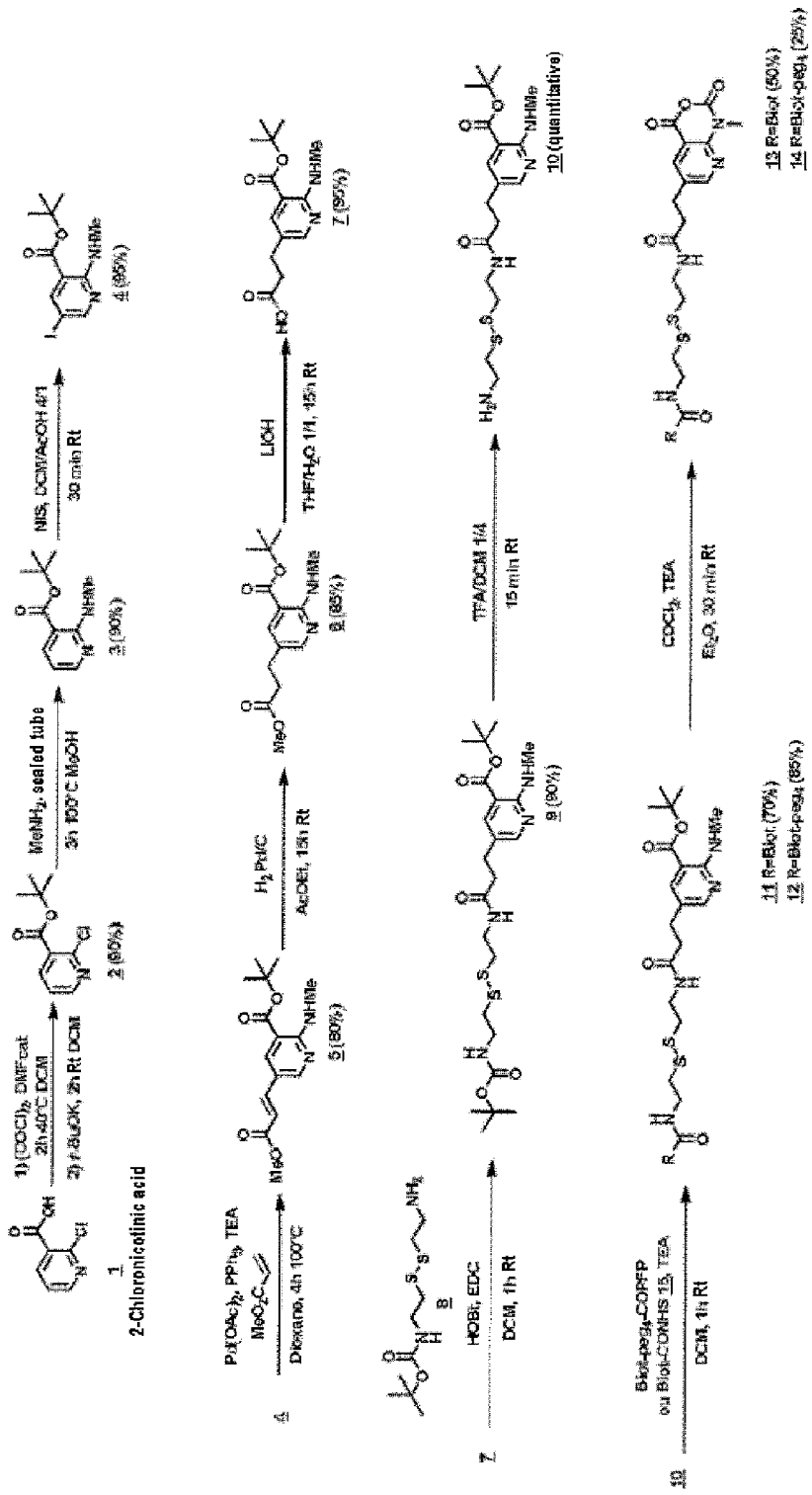

FIG. 3 describes the synthesis of an aza-isatoic derivative provided with a biotinylated group of interest.

Figure 4:
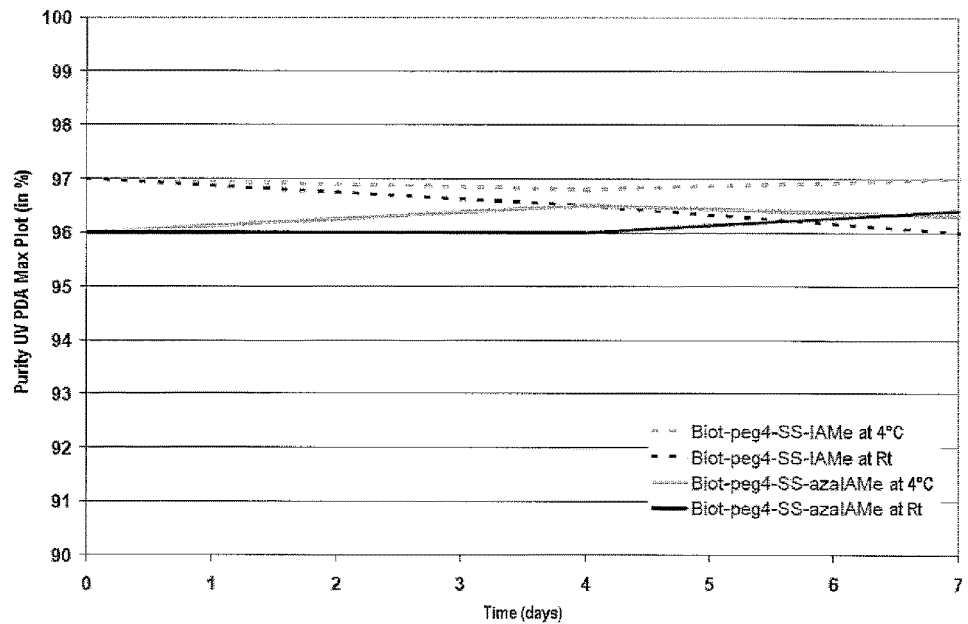

FIG. 4 presents a graph for investigation of the stability of an aza-isatoic compound in solution compared to that of an isatoic compound.

Figure 5:
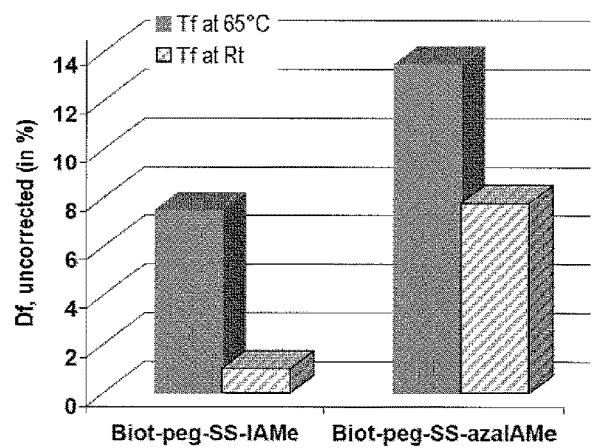

FIG. 5 shows a graph for functionalization tests of a 27-mer ORN with derivatives of isatoic and aza-isatoic anhydride.

Figure 6:
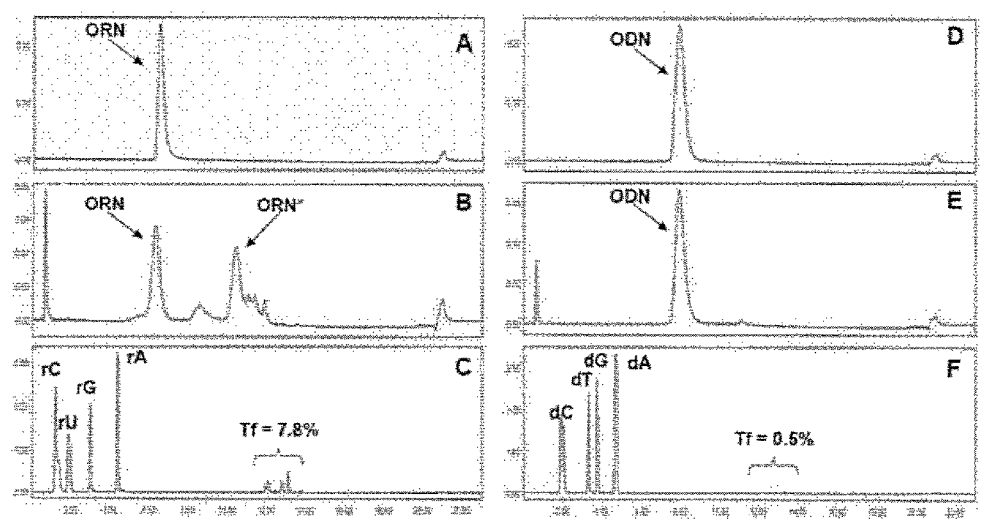

FIG. 6 aims to highlight the chemoselectivity of the aza-isatoic series for RNA relative to that of DNA.

The following abbreviations will be used in the examples described below:

RCN: acetonitrile,
EtOAc: ethyl acetate,
$Boc_2O$: di-tert-butyl bicarbonate,
DNA: deoxyribonucleic acid,
RNA: ribonucleic acid,
Biot-peg$_4$-COPFP: ester of 3-(2-(2-(3-biotin-dPEG$_3$-propanamido)ethyl)disulphanyl)propanoic acid and pentafluoro phenol
Biot-peg$_4$-SS-azaIAMe: molecule 14 of the present application (1-{5-[(3aS,6aR)-2-oxo-hexahydro-1H-thieno[3,4-d]imidazolidin-4-yl]pentanamido}-N-(2-{[2-(3-{1-methyl-2,4-dioxo-1H,2H,4H-pyrido[2,3-d][1,3]oxazin-6-yl}propanamido)ethyl]disulphanyl}ethyl)-3,6,9,12-tetraoxapentadecan-15-amide),
Biot-peg$_4$-SS-IAMe: 5-(3-(2-(2-(biotin-dPEG$_3$-propanamido)ethyl)disulphanyl))propanamido) isatoic anhydride, as described in example 1-10 of application WO-A-2012/076794,
TLC: thin-layer chromatography,
CDCl$_3$: deuterated chloroform,
d: doublet,
DCM: dichloromethane,
dd: doublet of doublets,
DMF: dimethylformamide,
DMSO: dimethylsulphoxide,
DMSO-d6: deuterated dimethylsulphoxide,
MilliQ water: Ultrapure water (Millipore, Molsheim, France),
EDC: 1-ethyl-3-(3-dimethylaminopropyl) carbodiimide,
Eq: equivalents,
PE: petroleum ether,
Et$_2$O: diethyl ether,
HPLC: high-performance liquid chromatography,
HOBt: hydroxybenzotriazole,
IA: isatoic anhydride,
IVT: transcribed in vitro
m: multiplet,
Me: methyl,
MeOH: methanol,
Nb exp: experiment repetition number,
nd: not determined,
NHS: N-hydroxysuccinimide,
NIS: N-iodosuccinimide,
NMO: N-methylmorpholine,
NP1: nuclease P1,
ODN: oligo-deoxyribonucleotide,
ORN: oligo-ribonucleotide,
AP: alkaline phosphatase,
PBS 1×: Phosphate Buffered Saline=(0.01 M $PO_4^-$, 0.0027 M KCl, 0.137 M NaCl, pH=7.4 at 25° C. ref. SIGMA 4417, Saint Louis, USA),
PFP: pentafluorophenol,
q: quadruplet,
Yld: yield,
Rf or TR: retention time,
NMR: nuclear magnetic resonance,
rpm: revolutions per minute,
s: singlet,
SS: disulphide bond,
t: triplet,
Rt or RT: room temperature,
TEAAc: triethylammonium acetate,
Df: degree of functionalization,
TFA: trifluoroacetic acid,
THF: tetrahydrofuran,
UV: ultraviolet.

The General Conditions for Analysis and Synthesis of the Chemical Compounds Used in the Following Examples are Described Below:

The LC-MS analyses were carried out with a WATERS Alliance 2795 HPLC chain equipped with a PDA 996 diode array detector (Waters), a ZQ 2000 mass spectrometry detector (Waters), Empower software version 2 and a WATERS XTerra MS C18 column (4.6×30 2.5 µm) used with a flow of 1 ml/min at 30° C. (detection at 260 nm or in max plot). The ZQ 2000 mass spectrometer has an electrospray ionization source. Ionizations were carried out in positive mode with a cone voltage of 20V and a voltage at capillary level of 3.5 kV.

The conditions used for the HPLC analyses are as follows (conditions 1):

TABLE 1

| Conditions used for the HPLC analyses | | | |
|---|---|---|---|
| Eluent A | Eluent B | Eluent C | Linear gradient |
| MilliQ water | Acetonitrile | Ammonium formate 500 mM pH 7 | 98% of A/0% of B to 24% of A/74% of B in 18 min with 2% of eluent C in isocratic mode |

The NMR spectra were recorded on a Jeol Lambda 400 MHz spectrometer or a Brüker Avance 500 MHz spectrometer. The chemical shifts (δ) are given in ppm relative to the peak of the solvent taken as internal reference ($CDCl_3$: 7.26 ppm; DMSO-d6: 2.49 ppm). The spectra are described with the above abbreviations: s, d, t, q, qu and m. The coupling constants (J) are expressed in hertz (Hz).

Column chromatography was carried out on silica gel Macherey-Nagel Kieselgel 60, 0.063-0.2 mm/70-230 mesh or Merck LiChroprep® RP-18 40-63 μm.

The analyses by thin-layer chromatography were carried out on Macherey-Nagel plates POLYGRAM® SIL G/UV254, 0.20 mm or ALUGRAM® RP-1B W/UV254 0.15 mm.

EXAMPLE 1: SYNTHESIS OF AN AZA-ISATOIC ANHYDRIDE DERIVATIVE CONJUGATED WITH A GROUP OF INTEREST

Introduction: General Specification of the Synthesis of the Compounds that Will be Described in Example 1.

Conjugation of the aza-isatoic anhydride or derivatives thereof with a group of interest assumes chemical reaction between the aza-isatoic anhydride, provided with a reactive function, and the molecule of interest, it too being provided with a reactive function. Note that it is particularly important to preserve the integrity of the aza-isatoic anhydride part during this coupling. A person skilled in the art knows a multitude of ways of conjugating two molecules together in this way in order to obtain a new molecule having properties common to both.

The strategy chosen for this synthesis is based on iodination in position 6 of chloronicotinic acid, protected in the form of tert-butyl ester 2, to obtain compound 4. This then allows insertion in position 6 of a precursor of a carboxylic acid function (compound 5), said function will be the point of attachment for introduction of a linkage and then a group of interest by means of couplings of the pseudo-peptide type. In a last step, formation of the aza-isatoic anhydride takes place by intramolecular cyclization of the tert-butyl amino ester 11 or 12 in the presence of phosgene, as is clearly shown in FIG. 3. This strategy makes it possible to work on stable precursors throughout the synthesis. The aza-isatoic anhydride, which is more fragile, is synthesized and purified only at the end. In the protocol allowing direct access to aza-isatoic anhydride starting from the tert-butyl amino ester, generally formation of the anhydride was carried out starting from the suitably substituted aza-anthranilate. Finally, this synthesis route is versatile and can be adapted to a great many linkages and groups of interest; the main advantage is the possibility of using a group of interest or a linkage or one of their baso-labile precursors.

EXAMPLE 1.1: SYNTHESIS OF TERT-BUTYL 2-CHLORONICOTINATE

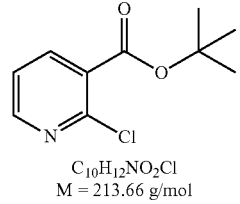

2

$C_{10}H_{12}NO_2Cl$
M = 213.66 g/mol

In a 250-mL flask, 5 g of 2-chloronicotinic acid (31.73 mmol; 1 eq) is dissolved in 100 mL of anhydrous THF. A volume of 5.37 mL of oxalyl chloride (63.47 mmol; 2 eq), and five drops of DMF are added successively to the reaction mixture at 0° C. This mixture is stirred magnetically at room temperature for 2 hours. The reaction mixture is then evaporated to dryness and the oil thus obtained is then dissolved in 100 mL of anhydrous THF. An amount of 4.27 g of tBuOK (38.08 mmol, 1.2 eq) is then added at −10° C., and the reaction mixture is stirred magnetically for 2 h at room temperature.

The reaction mixture is evaporated to dryness, taken up in 200 mL of a 5% aqueous solution of $K_2CO_3$, then extracted with dichloromethane (3×150 mL). The organic phases are then combined, dried over anhydrous sodium sulphate, filtered, and finally evaporated. The end product is obtained in the form of oil at a yield of 88% (5.97 g; 27.94 mmol).

IR (KBr): ν 1732 (C=O), 1579, 1403, 1370, 1315, 1288, 1173, 1144, 1065, 1056 $cm^{-1}$.

$^1$H NMR (400 MHz, $CDCl_3$): δ 1.62 (s, 9H); 7.31 (dd, 1H, $^3J$=7.8 Hz, $^3J$=4.4 Hz); 8.07 (dd, 1H, $^3J$=7.8 Hz, $^4J$=1.9 Hz); 7.31 (dd, 1H, $^3J$=4.4 Hz, $^4J$=1.9 Hz).

$^{13}$C NMR (100 MHz, $CDCl_3$): δ 28.0 (30); 83.3; 122.0; 128.8; 139.8; 149.4; 151.2; 163.9.

HRMS (ESI) theoretical $C_{10}H_{12}NO_2Cl$ [M+H]$^+$ 214.0635; experimental 214.0638.

EXAMPLE 1.2: SYNTHESIS OF TERT-BUTYL 2-(METHYLAMINO)NICOTINATE

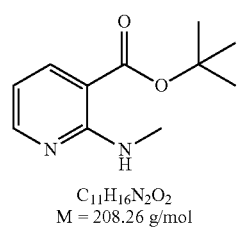

3

$C_{11}H_{16}N_2O_2$
M = 208.26 g/mol

In a 30-mL sealed tube, 2.82 g of tert-butyl 2-chloronicotinate 2 (13.20 mmol; 1 eq) is dissolved in 4.6 mL of methanol. 4.6 mL of a 40% aqueous solution of methylamine (53.26 mmol; 4 eq) is added to the reaction mixture at room temperature. The reaction is stirred magnetically at 100° C. for 2 hours.

The reaction mixture is evaporated to dryness, taken up in 75 mL of water, then extracted with dichloromethane (3×75 mL). The organic phases are then combined, dried over anhydrous sodium sulphate, filtered, and finally evaporated. The oil obtained is then purified on a silica gel column using a gradient of eluent (PE then PE/Et$_2$O 9.5:0.5). The end product is obtained in the form of oil at a yield of 85% (2.35 g; 11.28 mmol).

IR (KBr): ν 3380 (NH), 1684 (C=O), 1595, 1583, 1520, 1392, 1305, 1262, 1250, 1172, 1126 cm$^{-1}$.

$^1$H NMR (400 MHz, CDCl$_3$): δ 1.57 (s, 9H); 3.05 (d, 3H, $^3$J=4.9 Hz); 6.49 (dd, 1H, $^3$J=7.5 Hz, $^3$J=4.4 Hz); 7.98 (si, 1H); 8.04 (dd, 1H, $^3$J=7.5 Hz, $^4$J=2.0 Hz); 8.28 (dd, 1H, $^3$J=4.4 Hz, $^4$J=2.0 Hz).

$^{13}$C NMR (100 MHz, CDCl$_3$): δ 27.8; 28.2 (3C); 81.2; 107.5; 110.4; 139.9; 153.0; 159.3; 167.1.

HRMS (IE) theoretical C$_{11}$H$_{16}$N$_2$O$_2$ [M]$^+$ 208.1212; experimental 208.1213.

EXAMPLE 1.3: SYNTHESIS OF TERT-BUTYL 5-IODO-2-(METHYLAMINO)NICOTINATE

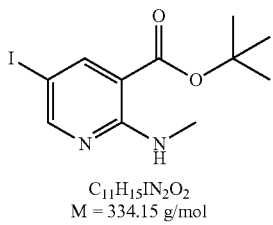

C$_{11}$H$_{15}$IN$_2$O$_2$
M = 334.15 g/mol

In a 100-mL flask, 4.5 g of tert-butyl 2-(methylamino) nicotinate 3 (21.61 mmol; 1 eq) is dissolved in 30 mL of a dichloromethane/acetic acid mixture (6:1). 5.83 g of N-iodosuccinimide (25.93 mmol; 1.2 eq) is added to the reaction mixture at room temperature. The reaction is stirred magnetically at room temperature for 30 minutes.

The reaction mixture is then neutralized with 7 mL of an aqueous saturated solution of sodium thiosulphate, taken up in 100 mL of a 5% aqueous solution of K$_2$CO$_3$, then extracted with dichloromethane (3×100 mL). The organic phases are then combined, dried over anhydrous sodium sulphate, filtered, and finally evaporated. The solid obtained is then purified on a silica gel column using a gradient of eluent (PE then PE/Et$_2$O 9:1). The end product is obtained in the form of yellow powder at a yield of 96% (6.92 g; 20.71 mmol).

m.p.: 101° C.

IR (KBr): ν 3371 (NH), 1679 (C=O), 1588, 1569, 1505, 1367, 1307, 1243, 1167, 1140, 1107, 796 cm$^{-1}$.

$^1$H NMR (400 MHz, CDCl$_3$): δ 1.57 (s, 9H); 3.01 (d, 3H, $^3$J=4.9 Hz); 7.97 (sl, 1H); 8.21 (d, 1H, $^4$J=2.0 Hz); 8.40 (d, 1H, $^4$J=2.0 Hz).

$^{13}$C NMR (100 MHz, CDCl$_3$): δ 27.8; 28.2 (3C); 73.1; 82.0; 109.8; 146.8; 157.9; 158.3; 166.0.

HRMS (IE) theoretical C$_{11}$H$_{15}$N$_2$O$_2$I [M]$^+$ 334.0179; experimental 334.0167.

EXAMPLE 1.4: SYNTHESIS OF TEXT-BUTYL 5-[(1E)-3-METHOXY-3-OXOPROP-1-IN-1-YL]-2-(METHYLAMINO)NICOTINATE

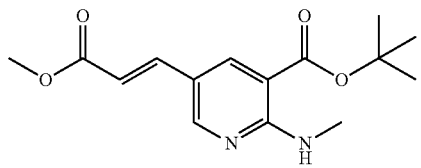

C$_{15}$H$_{20}$N$_2$O$_4$
M = 292.33 g/mol

In a 250-mL flask, 394 mg of triphenylphosphine (1.50 mmol; 0.1 eq), 168 mg of palladium acetate (0.75 mmol; 0.05 eq) and 2.08 mL of triethylamine (14.96 mmol, 1 eq) are dissolved in 50 mL of dioxane previously degassed under nitrogen. The mixture is stirred magnetically at 100° C. for 5 minutes. 5 g of the iodinated derivative 4 (14.96 mmol; 1 eq) and 6.74 mL of methyl acrylate (74.82 mmol; 5 eq) are then added and the reaction is stirred magnetically at 100° C. for 4 hours.

The reaction mixture is evaporated to dryness, taken up in 50 mL of dichloromethane and then filtered on Celite. 200 mL of water is added and the mixture is extracted with dichloromethane (3×150 mL). The organic phases are then combined, dried over anhydrous sodium sulphate, filtered, and finally evaporated. The solid obtained is then purified on a silica gel column using a gradient of eluent (PE to PE/Et$_2$O 7 3). The end product is obtained in the form of yellow powder at a yield of 76% (3.33 g; 11.39 mmol).

m.p.: 114° C.

IR (KBr): ν 3373 (NH), 1720 (C=O), 1693 (C=O), 1634, 1604, 1585, 1526, 1317, 1266, 1253, 1203, 1188, 1161, 1134 cm$^{-1}$.

$^1$H NMR (400 MHz, CDCl$_3$): δ 1.59 (s, 9H); 3.09 (d, 33, $^3$J=4.9 Hz); 3.80 (s, 3H); 6.27 (d, 1H, $^3$J=15.8 Hz); 7.59 (d, 1H, $^3$J=15.8 Hz); 8.22 (d, 1H, $^4$J=2.4 Hz); 8.30 (sl, 1H); 8.41 (d, 1H, $^4$J=2.4 Hz).

$^{13}$C NMR (100 MHz, CDCl$_3$): δ 28.0; 28.2 (3C); 51.5; 82.1; 107.7; 113.7; 117.6; 138.2; 141.2; 153.9; 159.6; 166.5; 167.6.

HRMS (IE) theoretical C$_{15}$H$_{20}$N$_2$O$_4$ [M]$^+$ 292.1423; experimental 292.1413.

EXAMPLE 1.5: SYNTHESIS OF TERT-BUTYL 5-(3-METHOXY-3-OXOPROPYL)-2-(METHYLAMINO)NICOTINATE

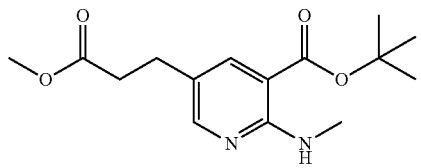

C$_{15}$H$_{22}$N$_2$O$_4$
M = 294.35 g/mol

In a 500-mL flask, 6 g of the vinylic derivative 5 (20.52 mmol; leg) is dissolved in 250 mL of ethyl acetate. 2.1 g of Pd/C is added and the reaction is stirred magnetically at room temperature under a hydrogen stream for 24 hours.

The reaction mixture is filtered on a Büchner and then on Celite, and finally is evaporated to dryness. The solid obtained is then purified on a silica gel column using a gradient of eluent (PE to PE/Et$_2$O 7:3). The end product is obtained in the form of yellow powder at a yield of 81% (4.88 g; 16.58 mmol).

m.p.: 69° C.

IR (KBr): ν 3392 (NH), 1736 (C=O), 1690 (C=O), 1574, 1520, 1371, 1227, 1194, 1173, 1156, 1127, 1090, 802 cm$^{-1}$.

$^1$H NMR (400 MHz, CDCl$_3$): δ 1.57 (s, 9H); 2.58 (t, 2H, $^3$J=7.8 Hz); 2.82 (t, 2H, $^3$J=7.8 Hz); 3.03 (d, 3H, $^3$J=4.9 Hz); 3.68 (s, 3E); 7.85 (sl, 1H); 7.87 (s, 1H); 8.14 (s, 1H).

$^{13}$C NMR (100 MHz, CDCl$_3$): δ 27.1; 27.9; 28.2 (3C); 35.8; 51.7; 81.4; 107.3; 122.0; 139.7; 152.7; 158.2; 167.0; 173.1.

HRMS (ESI) theoretical C$_{10}$H$_{22}$N$_2$O$_4$ [M+H]$^+$ 295.1658; experimental 295.1655.

EXAMPLE 1.6: SYNTHESIS OF 3-{5-[(TERT-BUTOXY)CARBONYL]-6-(METHYLAMINO)PYRIDIN-3-YL}PROPANOIC ACID

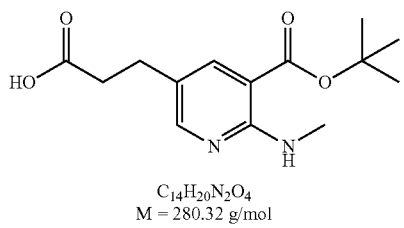

C$_{14}$H$_{20}$N$_2$O$_4$
M = 280.32 g/mol

In a 250-mL flask, 4.87 g of derivative 6 (16.54 mmol; 1 eq) is dissolved in 50 mL of tetrahydrofuran. 50 mL of a 1M aqueous solution of lithium hydroxide (50 mmol; 3 eq) is added and the reaction is stirred magnetically at room temperature for 45 minutes.

The reaction mixture is evaporated to remove the tetrahydrofuran. The pH of the aqueous solution obtained is adjusted to 6 with acetic acid. This solution is then extracted with ethyl acetate (4×50 mL). The organic phases are then combined, dried over anhydrous sodium sulphate, filtered, and finally co-evaporated with toluene. The end product is obtained in the form of yellow powder at a yield of 92% (4.25 g; 15.16 mmol).

m.p.: 106° C.

IR (KBr): ν 3374 (NH), 1713 (C=O), 1683 (C=O), 1584, 1538, 1367, 1342, 1304, 1282, 1245, 1192, 1169, 1139, 1101, 801 cm$^{-1}$.

$^1$H NMR (400 MHz, CDCl$_3$): δ 1.57 (s, 9H); 2.62 (d, 2H, $^3$J=7.8 Hz); 2.85 (t, 2H, $^3$J=7.8 Hz); 3.02 (t, 3H, $^3$J=4.9 Hz); 7.92 (d, 1H, $^4$J=2.0 Hz); 7.95 (sl, 1H); 8.20 (s, 1H).

$^{13}$C NMR (100 MHz, CDCl$_3$): δ 27.0; 28.1; 28.2 (3C); 35.9; 81.6; 107.8; 122.2; 140.5; 152.6; 157.9; 166.8; 177.0.

HRMS (ESI) theoretical C$_{14}$H$_{20}$N$_2$O$_4$ [M+H]$^+$ 281.1501; experimental 281.1500.

EXAMPLE 1.7: SYNTHESIS OF TERT-BUTYL N-{2-[(2-AMINOETHYL)DISULPHANYL]ETHYL}CARBAMATE

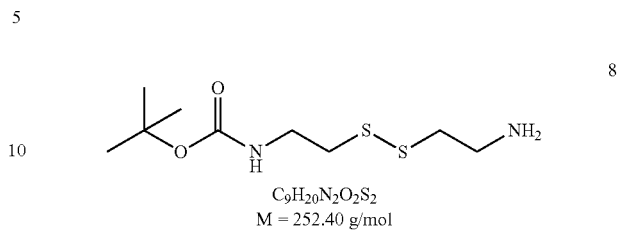

C$_9$H$_{20}$N$_2$O$_2$S$_2$
M = 252.40 g/mol

In a 250-mL flask, 6 g of cystamine (26.64 mmol; 1 eq) is dissolved in 50 mL of methanol. A solution of 5.814 g of Boc$_2$O (26.64 mmol; 1 eq) and 11.14 mL of TEA (79.12 mmol; 3 eq) in 40 mL of methanol is then added dropwise to the cystamine solution in the space of 45 minutes, with magnetic stirring at room temperature.

The reaction mixture is then evaporated to dryness, obtaining a white solid. The solid obtained is taken up in 70 mL of a 1M solution of NaH$_2$PO$_4$. The mixture is then extracted with diethyl ether (3×90 mL). The aqueous phase is alkalized to pH 9 using a 1M NaOH solution. The mixture is then extracted with ethyl acetate (6×50 mL). The organic phases are combined, dried over MgSO$_4$ and then evaporated under vacuum.

The product is obtained in the form of oil at a yield of 42% (2.82 g; 11.19 mmol).

IR (KBr): ν 3356 (NH), 2976, 2930, 1694 (CO), 1517, 1392, 1366, 1275, 1253, 1170 cm$^{-1}$.

$^1$H NMR (400 MHz, CDCl$_3$): δ 1.45 (s, 9H); 1.75 (s, 2H); 2.78 (m, 4H); 3.03 (m, 2H, J=5 Hz); 3.46 (m, 2H); 5.01 (s, 1H).

$^{13}$C NMR (100 MHz, CDCl$_3$): δ 38.1; 39.2; 40.1; 41.3; 79.4; 155.7.

EXAMPLE 1.8: SYNTHESIS OF TERT-BUTYL 5-[2-({2-[(2-{[(TERT-BUTOXY) CARBONYL]AMINO}ETHYL)DISULPHANYL]ETHYL}CARBAMOYL)ETHYL]-2-(METHYLAMINO)NICOTINATE

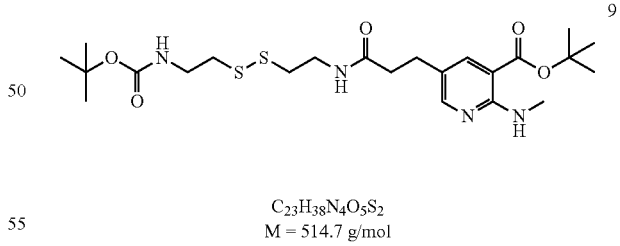

C$_{23}$H$_{38}$N$_4$O$_5$S$_2$
M = 514.7 g/mol

In a 250-mL flask, 3 g of the acid derivative 7 (10.70 mmol; 1 eq), 3.08 g of EDC (16.06 mmol; 1.5 eq) and 2.17 g of HOBt (16.06 mmol; 1.5 eq) are dissolved in 50 mL of dichloromethane. After 10 minutes at room temperature, 2.97 g of the amino derivative 8 is then added, and the reaction is stirred at room temperature for 2 hours.

The reaction mixture is evaporated to dryness, taken up in 75 mL of a saturated aqueous sodium bicarbonate solution and then extracted with ethyl acetate (4×75 mL). The organic phases are then combined, dried over anhydrous sodium sulphate and filtered. The solid obtained is then purified on a silica gel column using a gradient of eluent (DCM/EtOAc 8/2 to DCM/EtOAc 2/8). The end product is obtained in the form of white powder at a yield of 94% (5.2 g; 10.10 mmol).

m.p.: 106° C.

IR (KBr): ν 3385 (NH), 3338 (NH), 3275 (NH), 1682 (C=O), 1654 (C=O), 1569, 1547, 1538, 1511, 1389, 1366, 1303, 1289, 1253, 1229, 1165, 1126 cm$^{-1}$.

$^1$H NMR (400 MHz, CDCl$_3$): δ 1.43 (s, 9H); 1.57 (s, 9H); 2.47 (t, 2H, $^3$J=7.5 Hz); 2.74 (t, 2H, $^3$J=6.8 Hz); 2.83 (m, 4H); 3.03 (d, 3H, $^3$J=4.9 Hz); 3.42 (q, 2H, $^3$J=6.4 Hz); 3.55 (q, 2H, $^3$J=5.8 Hz); 5.03 (sl, 1H); 6.51 (sl, 1H); 7.84 (sl, 1H); 7.87 (d, 1H, $^4$J=1.3 Hz); 8.14 (d, 1H, $^4$J=1.3 Hz).

$^{13}$C NMR (100 MHz, CDCl$_3$): δ 27.9 (2C); 28.2 (3C); 28.3 (3C); 37.4; 38.0; 38.3; 38.5; 39.5; 79.7; 81.3; 107.2; 122.4; 139.8; 152.8; 155.9; 158.2; 167.0; 172.2.

HRMS (ESI) theoretical C$_{23}$H$_{38}$N$_4$O$_5$S$_2$ [M+H]$^+$ 515.2362; experimental 515.2342.

EXAMPLE 1.9: SYNTHESIS OF TERT-BUTYL 5-[2-({2-[(2-AMINOETHYL)DISULPHANYL] ETHYL}CARBAMOYL)ETHYL]-2-(METHYL-AMINO)NICOTINATE

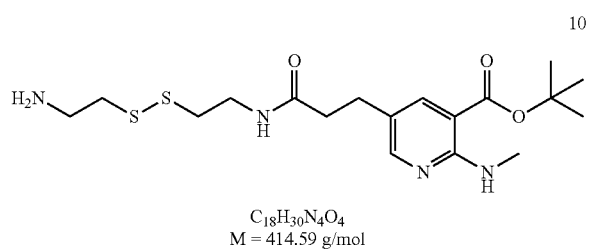

10

C$_{18}$H$_{30}$N$_4$O$_4$
M = 414.59 g/mol

In a 100-mL flask under nitrogen, 2 g of derivative 9 (3.89 mmol; 1 eq) is dissolved in 15 mL of dichloromethane. 5 mL of trifluoroacetic acid (65.29; 16.8 eq) is added, and the reaction is stirred magnetically at room temperature for 30 minutes.

The reaction mixture is evaporated to dryness, taken up in 50 mL of saturated aqueous sodium bicarbonate solution, and then extracted with ethyl acetate (4×50 mL). The organic phases are then combined, washed with water (2×50 mL), dried over anhydrous sodium sulphate and filtered. The end product is obtained in the form of oil at a quantitative yield (1.6 g; 3.86 mmol)

IR (KBr): ν 3378 (NH), 2977, 2931, 1682 (CO), 1612, 1578, 1520, 1368, 1304, 1228, 1160, 1131, 1095, 910, 732 cm$^{-1}$. .

$^1$H NMR (400 MHz, CDCl$_3$): δ 1.58 (s, 9H); 1.64 (sl, 2H); 2.42 (t, 2H, $^3$J=7.6 Hz); 2.76 (t, 4H, $^3$J=6.1 Hz); 2.84 (t, 4H, $^3$J=7.6 Hz); 3.03 (d, 3H, $^3$J=4.9 Hz); 3.03 (m, 2H); 3.58 (q, 2H, $^3$J 6.1 Hz); 6.00 (sl, 1H); 7.84 (sl, 1H); 7.87 (d, 1H $^4$J=2.4 Hz); 8.14 (d, 1H, $^4$J=2.4 Hz).

$^{13}$C NMR (100 MHz, CDCl$_3$): δ 27.7; 27.8; 28.1 (30); 37.4; 37.9; 38.3; 40.3; 41.9; 81.3; 107.1; 122.2; 139.7; 152.5; 158.0; 166.8; 171.9.

HRMS (ESI) theoretical C$_{18}$H$_{30}$N$_4$O$_3$S$_2$ [M+H]$^+$ 415.1838; experimental 415.1821.

EXAMPLE 1.10: SYNTHESIS OF TERT-BUTYL 5-[2-({2-[(2-{5-[(3AS,6AR)-2-OXO-HEXA-HYDRO-1H-THIENO[3,4-D]IMIDAZOLIDIN-4-YL]PENTANAMIDO}ETHYL)DISULPHANYL] ETHYL}CARBAMOYL)ETHYL]-2-(METHYLAMINO)NICOTINATE

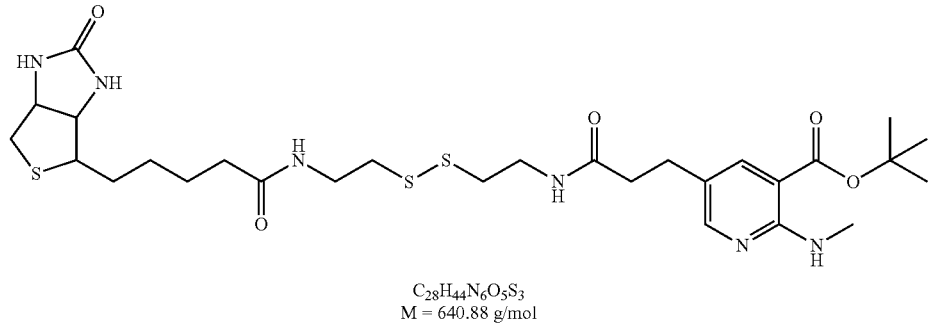

11

C$_{28}$H$_{44}$N$_6$O$_5$S$_3$
M = 640.88 g/mol

In a 100-mL flask, 500 mg of the amino derivative 10 (1.21 mmol, 1 eq) is dissolved in 20 mL of anhydrous dimethylformamide. 412 mg of Biot-CONHS (15, 1.21 mmol; 1 eq) and 168 μL of triethylamine (1.21 mmol; 1 eq) are added, and the reaction is stirred magnetically at room temperature for 1 hour.

The reaction mixture is evaporated to dryness and directly purified on a grafted C18 silica gel column, using a gradient of eluent (H$_2$O to H$_2$O/ACN 3/7). The end product is obtained in the form of white powder at a yield of 70% (545 mg; 0.85 mmol).

m.p.: 108° C.

IR (KBr): ν 3297 (NH), 3074, 2928, 2853, 1704 (CO), 1683 (CO), 1642 (CO), 1613, 1578, 1520, 1226, 1159, 1094, 803, 727, 597 cm$^{-1}$.

$^1$H NMR (500 MHz, DMSO-d6): δ 1.42 (m, 2H); 1.57 (s, 9H); 1.60-1.73 (m, 4H); 2.23 (td, 2H, $^4$J=2.9 Hz, $^3$J=7.2 Hz); 2.47 (t, 2H, $^3$J=7.5 Hz); 2.71 (d, 1H, $^2$J=12.8 Hz); 2.78-2.88 (m, 6H); 2.89 (dd, 1H, $^3$J=4.9 Hz, $^2$J=12.8 Hz); 3.01 (d, 3H, $^3$J=4.9 Hz); 3.10-3.15 (m, 1H); 3.50-3.54 (m, 4H); 4.30 (dd, 1H, $^3$J=4.5 Hz, $^3$J=7.5 Hz); 4.50 (dd, 1H, $^3$J=4.9 Hz, $^3$J=7.5 Hz); 5.71 (sl, 1H); 6.58 (sl, 1H); 6.85 (t, 1H, $^3$J=5.8 Hz); 7.09 (t, 1H, $^3$J=5.8 Hz); 7.83 (q, 1H, $^3$J=4.9 Hz); 7.88 (d, 1H $^4$J=2.4 Hz); 8.14 (d, 1H, $^4$J=2.4 Hz).

$^{13}$C NMR (125 MHz, DMSO-d6): δ 25.6; 27.9; 27.9; 28.0; 28.1; 28.3 (3C); 35.7; 37.6; 38.0; 38.2; 38.4; 38.5; 40.6; 55.7; 60.2; 61.7; 81.5; 107.4; 122.6; 140.0; 152.6; 158.2; 164.1; 167.0; 172.6; 173.8.

HRMS (ESI) theoretical C$_{28}$H$_{44}$N$_6$O$_5$S$_3$ [M+H]$^+$ 641.2614; experimental 641.2626.

EXAMPLE 1.11: SYNTHESIS OF 5-[(3AS,6AR)-2-OXO-HEXAHYDRO-1H-THIENO[3,4-D]IMIDAZOLIDIN-4-YL]-N-(2-{[2-(3-{1-METHYL-2,4-DIOXO-1H,2H,4H-PYRIDO[2,3-D][1,3]OXAZIN-6-YL}PROPANAMIDO)ETHYL]DISULPHANYL}ETHYL)PENTANAMIDE

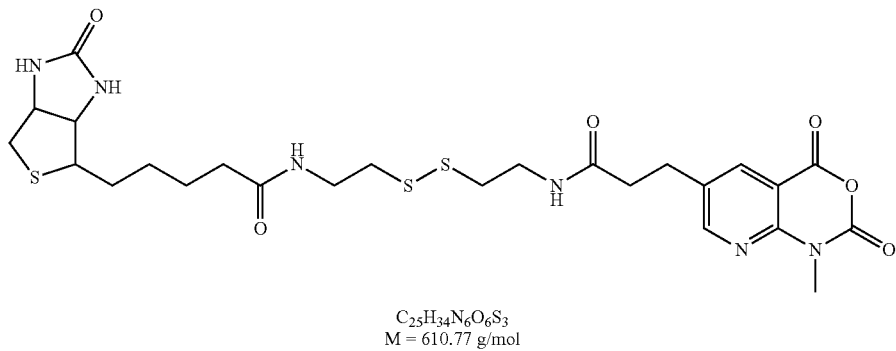

12

$C_{25}H_{34}N_6O_6S_3$
M = 610.77 g/mol

In a 30-mL sealed tube, 500 mg of derivative 11 (0.78 mmol; leg) is dissolved in 20 mL of diethyl ether. 1.23 mL of a 20% phosgene solution in toluene (2.34 mmol; leg) and 325 μL of triethylamine (2.34 mmol; 3 eq) are added, and the reaction is stirred magnetically at room temperature for 30 minutes.

The reaction mixture is evaporated to dryness and directly purified on a grafted C18 silica gel column, using a gradient of eluent ($H_2O$ to $H_2O$/ACN 4/6). The end product is obtained in the form of white powder at a yield of 42% (200 mg; 0.33 mmol).

m.p.: 125° C.

IR (KBr): ν 3299 (NH), 2927, 1785 (CO), 1735 (CO), 1704 (CO), 1641 (CO), 1612, 1488, 1326, 1232, 1179, 1069, 1045, 979, 787, 745, 674 $cm^1$.

$^1$H NMR (500 MHz, DMSO-d6): δ 1.24-1.34 (m, 2H); 1.41-1.59 (m, 4H); 2.05 (t, $^3J$=7.4 Hz, 2H); 2.44 (t, 2H, $^3J$=7.4 Hz); 2.56 (d, 1H, $^2J$=12.4 Hz); 2.68-2.73 (m, 4H); 2.80 (dd, 1H, $^3J$=5.0 Hz, $^2J$=12.4 Hz); 2.90 (t, 2H, $^3J$=7.4 Hz); 3.26-3.29 (m, 4H); 3.47 (s, 3H); 4.11 (m, 1H); 4.28 (m, 1H); 6.35 (sl, 1H); 6.41 (sl, 1H); 7.97 (t, 1H, $^3J$=5.5 Hz); 8.06 (t, 1H, $^3J$=5.5 Hz); 8.21 (d, 1H, $^4J$=2.2 Hz); 8.62 (d, 1H, $^4J$=2.2 Hz).

$^{13}$C NMR (125 MHz, DMSO-d6): δ 25.2; 26.9; 27.9; 28.1; 29.9; 35.1; 36.0; 37.2 (2C); 37.8; 37.8; 39.8; 55.4; 59.2; 61.0; 107.2; 132.7; 137.8; 147.7; 150.9; 155.4; 158.4; 162.7; 170.9; 172.2.

HRMS (ESI) theoretical $C_{25}H_{34}N_6O_6S_3$ $[M+H]^+$ 611.1780; experimental 611.1777.

EXAMPLE 1.12: SYNTHESIS OF TERT-BUTYL 5-{2-[(2-{[2-(1-{5-[(3AS,6AR)-2-OXO-HEXAHYDRO-1H-THIENO[3,4-D]IMIDAZOLIDIN-4-YL]PENTANAMIDO}-3,6,9,12-TETRAOXAPENTADECAN-15-AMIDO)ETHYL]DISULPHANYL}ETHYL)CARBAMOYL]ETHYL}-2-(METHYLAMINO) NICOTINATE

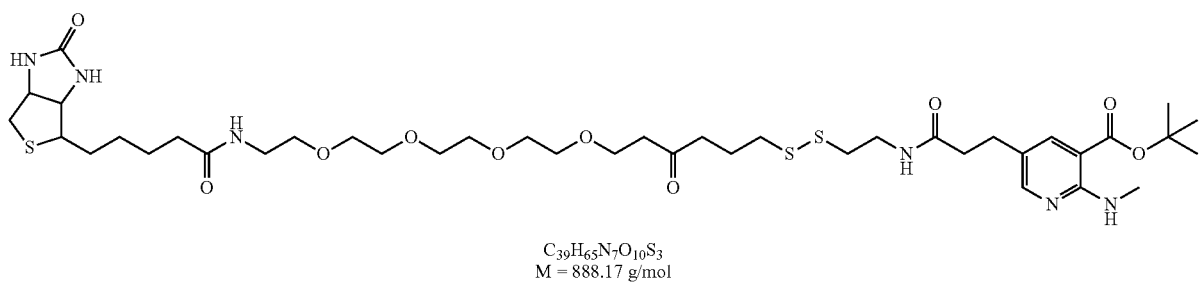

13

$C_{39}H_{65}N_7O_{10}S_3$
M = 888.17 g/mol

In a 100-mL flask, 400 mg of the amino derivative 10 (0.965 mmol; leg) is dissolved in 15 mL of dichloromethane. 635 mg of Biot-peg$_4$-COPFP (0.965 mmol; 1 eq, QuantaBioDesign, Powell, USA) and 134 μL of triethylamine (0.965 mmol; 1 eq) are added, and the reaction is stirred magnetically at room temperature for 45 minutes.

The reaction mixture is evaporated to dryness and directly purified on a grafted 018 silica gel column, using a gradient of eluent ($H_2O$ to $H_2O$/ACN 4/6). The end product is obtained in the form of white powder at a yield of 85% (730 mg; 0.822 mmol).

IR (KBr): ν 3400 (NH), 2925, 1681 (CO), 1644 (CO), 1579, 1525, 1157, 1124, 804, 618 $cm^{-1}$.

$^1$H NMR (500 MHz, DMSO-d6): δ 1.40-1.46 (m, 2H); 1.57 (s, 9H); 1.61-1.78 (m, 4H); 2.22 (t, 2H, $^3J$=7.1 Hz);

2.46-2.49 (m, 4H); 2.73 (d, 1H, $^2J$=12.7 Hz); 2.77-2.83 (m, 6H); 2.90 (dd, $^3J$=5.0 Hz, 1H, $^2J$=12.7 Hz); 3.02 (d, 3H, $^3J$=4.9 Hz); 3.13 (m, 1H); 3.39-3.44 (m, 2H); 3.52-3.55 (m, 6H); 3.62-3.63 (m, 12H); 3.72 (t, 2H, $^3J$=5.9 Hz); 4.31 (m, 1H); 4.50 (m, 1H); 5.41 (sl, 1H); 6.33 (sl, 1H); 6.85 (t, 1H, $^3J$=5.5 Hz); 6.95 (t, 1H, $^3J$=5.6 Hz); 7.28 (t, 1H, $^3J$=5.8 Hz); 7.82 (q, 1H, $^3J$=4.9 Hz); 7.88 (d, 1H, $^4J$=2.5 Hz); 8.14 (d, 1H, $^4J$=2.5 Hz).

$^{13}$C NMR (125 MHz, DMSO-d6): δ 24.6; 26.9; 26.9; 27.1; 27.1; 27.3 (3C); 34.8; 35.8; 36.2; 37.2; 37.3; 37.4; 37.5; 38.2; 39.5; 54.5; 59.1; 60.8; 66.2; 68.9; 69.0; 69.2; 69.3; 69.5 (3C); 80.4; 106.3; 121.7; 138.9; 151.8; 157.2; 162.7; 166.1; 171.0; 171.5; 172.3.

HRMS (ESI) theoretical $C_{39}H_{65}N_7O_{10}S_3$ $[M+H]^+$ 888.4033; experimental 888.4020.

EXAMPLE 1.13: SYNTHESIS OF 1-{5-[(3AS, 6AR)-2-OXO-HEXAHYDRO-1H-THIENO[3,4-D] IMIDAZOLIDIN-4-YL]PENTANAMIDO}-N-(2-{ [2-(3-{1-METHYL-2,4-DIOXO-1H,2H,4H-PYRIDO[2,3-D][1,3]OXAZIN-6-YL}PROPANAMIDO)ETHYL] DISULPHANYL}ETHYL)-3,6,9,12-TETRAOXAPENTADECAN-15-AMIDE

14

$C_{36}H_{55}N_7O_{11}S_3$
M = 858.06 g/mol

In a 30-mL sealed tube, 200 mg of derivative 13 (225 μmol; 1 eq) previously adsorbed on 500 mg of C18 grafted silica is dissolved in 20 mL of diethyl ether. 355 μL of a 20% phosgene solution in toluene (675 μmol; 1 eq) and 94 μL of triethylamine (675 μmol; 3 eq) are added, and the reaction is stirred magnetically at room temperature for 30 minutes.

The reaction mixture is evaporated to dryness and directly purified on a grafted C18 silica gel column, using a gradient of eluent (H$_2$O to H$_2$O/ACN 4/6). The end product is obtained in the form of white powder at a yield of 26% (50 mg; 58.2 μmol).

IR (KBr): ν, 3426 (NH), 2926, 2875, 1782 (CO), 1729 (CO), 1641 (CO), 1550, 1490, 1369, 1330, 1093, 788, 746, 677 cm$^{-1}$.

$^1$H NMR (500 MHz, DMSO-d6): δ 1.41-1.47 (m, 2H); 1.58-1.78 (m, 4H); 2.23 (t, 2H, $^3J$=7.4 Hz); 2.49 (t, 2H, $^3J$=5.7 Hz); 2.64 (t, 2H, $^3J$=7.2 Hz); 2.75 (m, 3H); 2.78 (t, 2H, $^3J$=5.9 Hz); 2.91 (dd, 1H, $^3J$=4.9 Hz, $^2J$=12.5 Hz); 3.05 (t, 2H, $^3J$=7.2 Hz); 3.15 (m, 1H); 3.39-3.45 (m, 2H); 3.46-3.51 (m, 4H); 3.56 (t, 2H, $^3J$=5.0 Hz); 3.63-3.64 (m, 12H); 3.66 (s, 3H); 3.74 (t, 2H, $^3J$=5.7 Hz); 4.33 (m, 1H); 4.52 (m, 1H); 5.51 (sl, 1H); 6.37 (sl, 1H); 6.90 (t, 1H, $^3J$=5.4 Hz); 7.38 (t, 1H, $^3J$=5.7 Hz); 7.49 (t, 1H, $^3J$=5.7 Hz); 8.29 (d, 1H, $^4J$=2.2 Hz); 8.60 (d, 1H, $^4J$=2.2 Hz).

$^{13}$C NMR (125 MHz, DMSO-d6): δ 24.6; 26.7; 27.0; 27.1; 29.4; 34.8; 35.6; 35.7; 35.8; 37.1; 37.6; 37.7; 38.2; 39.5; 54.5; 59.2; 60.8; 64.8; 66.2; 68.9; 69.0; 69.1; 69.2; 69.4 (2C); 105.8; 132.3; 137.7; 146.8; 150.1; 155.5; 157.1; 162.8; 170.8; 171.2; 172.4.

HRMS (ESI) theoretical $C_{35}H_{56}N_7O_{11}S_3$ $[M+H]^+$ 858.3200; experimental 858.3185.

EXAMPLE 1.14: SYNTHESIS OF BIOT-CONHS

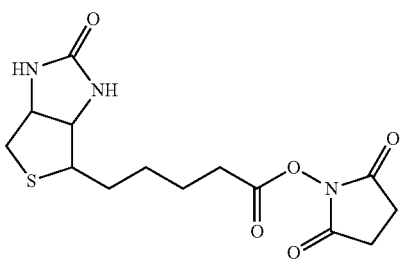

$C_{14}H_{19}N_3O_5S$
M = 341.38 g/mol

In a 100-mL flask, 2.5 g of D-biotin (10.23 mmol; 1 eq) and 1.18 g of N-hydroxysuccinimide (10.23 mmol; 1 eq) are dissolved in 40 mL of anhydrous dimethylformamide. The reaction is stirred magnetically at 70° C. until the reagents have dissolved completely. 2.55 g of EDC (13.30 mmol; 1.3 eq) is then added, and the reaction mixture is stirred at room temperature for 12 h.

The mixture is evaporated to dryness and then taken up in 30 mL of methanol. The precipitate obtained is then filtered on a frit, and then washed with MeOH (3×30 mL) and diethyl ether (3×90 mL).

The product is obtained in the form of white powder at a yield of 70% (2.46 g; 7.21 mmol).

m.p.: 210° C.

IR (KBr): ν 3234; 1820; 1789; 1747 (CO); 1730 (CO); 1705 (CO); 1216; 1072 cm$^{-1}$.

$^1$H NMR (400 MHz, DMSO-d$_6$): δ 1.39-1.67 (m, 6H); 2.57 (m, 1H); 2.66 (t, 2H, $^3J$=7.3 Hz); 2.68 (s, 4H); 2.84 (m, 1H); 3.09 (m, 1H); 4.14 (m, 1H); 4.29 (m, 1H); 6.37 (s, 1H); 6.43 (s, 1H).

$^{13}$C NMR (100 MHz, DMSO-d$_6$): δ 24.3; 25.5 (2C); 27.6; 27.9; 30.0; 39.9; 55.3; 59.1; 61.0; 162.8; 169.0; 174.4 (2C).

Results and Conclusion:

It is demonstrated in this example that the synthesis of an aza-isatoic derivative provided with a group of interest is feasible.

EXAMPLE 2: DEMONSTRATION OF THE STABILITY IN SOLUTION OF AN AZA-ISATOIC COMPOUND PROVIDED WITH A GROUP OF INTEREST

Objective:

Several tests intended to verify and demonstrate the chemical stability of the aza-isatoic derivative 14 relative to the reference compound Biot-peg$_4$-SS-IAMe as described in application FR 1060102 were carried out. These comparative tests were carried out in solution in DMSO at room temperature and at 4° C.

Procedure:

For each isatoic derivative, two solutions at 120 mM in DMSO were prepared and stored respectively at room temperature and at +4° C. for two weeks. For each of the solutions, three LC-MS analyses (condition 1) were performed at t=0, t=4 days and t=7 days. For each analysis, the purity of the compound is determined in UV PDA Max Plot, by integration of the peak corresponding to the isatoic derivative as well as any peaks corresponding to the degradation products. FIG. 4 presents the results obtained.

Results and Conclusion:

The results obtained show that the two isatoic derivatives do not degrade over time. No degradation product was detected in these experiments. They are therefore stable in solution in DMSO, not only at 4° C. but also at room temperature, for at least 7 days. We have thus demonstrated maintenance of chemical stability in the aza-isatoic series.

A person skilled in the art might think that the aza-isatoic molecule, being more reactive, would therefore be less stable. Now, surprisingly, example 2 demonstrates that this is not so, quite the contrary, the molecule remains perfectly stable over time at room temperature despite being more reactive (see also example 3, dealing with labelling).

EXAMPLE 3: DEMONSTRATION OF THE REACTIVITY AT ROOM TEMPERATURE OF AN AZA-ISATOIC COMPOUND, VERSUS A MODEL OLIGORIBONUCLEOTIDE (ORN) WITH 27 BASES—MEASUREMENT OF THE DEGREE OF FUNCTIONALIZATION

Objective:

In order to demonstrate the increase in reactivity in the aza-isatoic series, comparative tests of functionalization of a 27-mer ORN at room temperature and at 65° C. were conducted for the reference isatoic derivative, Biot-peg$_4$-SS-IAMe and for the aza-isatoic derivative, Biot-peg$_4$-SS-azaIAMe (14).

A comparison of the reactivity of the aza-isatoic anhydride derivative 14 relative to the reference isatoic derivative, Biot-peg$_4$-SS-IAMe as described in WO-A-2012/076794, with respect to a 27-base model ORN (seq: 5'-AAC-CGC-AGU-GAC-ACC-CUC-AUC-AUU-ACA-3', Eurogentec, Liege Science Park, Belgium) is carried out. For this, a fixed amount of ORN is reacted with an isatoic anhydride derivative conjugated with a molecule of interest, at 65° C. and at room temperature. The reaction is monitored by HPLC at 260 nm as was described previously in patent application WO-A-2012/076794 in example 3. This analysis makes it possible to detect the disappearance of the peak corresponding to the initial ORN and the appearance of peaks corresponding to the acylated ORN. These products have a greater retention time, and an absorption spectrum corresponding both to that of the ORN, and to that of the functionalizing reagent.

For precise evaluation of the degree of functionalization (Df), the ORN population (labelled and unlabelled) is separated from the surplus marker by precipitation with acetone/lithium perchlorate. Then the ORNs thus obtained are submitted to hydrolysis with nuclease P1 (Aldrich, Saint Louis, USA) and with alkaline phosphatase (Aldrich, Saint Louis, USA) in order to hydrolyse the phosphate diester bonds of the ORN.

LC-MS analysis of this mixture then allows several populations to be characterized and identified:
- unlabelled ribonucleosides;
- labelled mono-nucleoside adducts, which differ very clearly by a longer retention time, and by a UV spectrum characteristic of the nucleic acids and of the functionalizing reagent;
- dinucleotides acylated at 2' which, because of the anthranilate group substituted with the group of interest at 2', cannot be cleaved by the nuclease P1;
- per-acylated 2'OH trinucleotides or tetranucleotides, which may form theoretically but which are statistically very little represented (as this would then require two or three consecutive acylations of 2'OH), are not investigated.

Note that the 5'-O-acylated derivative is only very little represented and is not visible, as described by Servillo (Eur. J. Biochem. 1993 583-589).

The degree of functionalization of the ORN (Df) is evaluated by measuring:
- the area corresponding to the terminal mononucleoside adducts (functionalized at 2' and at 3') and the area corresponding to the acylated dinucleotides (functionalized internally on the 2'OH)
- compared to the area of the peaks corresponding to the four ribonucleosides.

Procedure:

In a standard experiment, the equivalent of 8 nmol of an ORN with 27 bases (5'-AAC-CGC-AGU-GAC-ACC-CUC-AUC-AUU-ACA-3', Eurogentec, Liege Science Park, Belgium) in solution in water is first dried in a centrifugal evaporator (RCT 60, Jouan, St Herblain, France) in a 2-mL plastic Eppendorf tube. The dry residue obtained is first dissolved in 40 μL of water, then 20 μl of a buffered solution is added (in the example, a 1M triethylammonium acetate buffer solution, pH 7, Aldrich, St Louis, USA ref: 09748-100 ml). Finally, 20 μl of a solution of an isatoic anhydride derivative at 120 mM in DMSO is incorporated in the preceding solution (either the reference molecule Biot-peg$_4$-SS-IAMe as described in FR 1060102 or the aza-isatoic derivative Biot-peg$_4$-SS-azaIAMe (14) in this example). The mixture is incubated for 60 minutes at room temperature or at 65° C. in a stove on a rack pre-equilibrated in temperature. To remove the salts and the surplus marker, the mixture is then purified by triple precipitation in 1.2 mL of an acetone/LiClO$_4$ 180 mM 75/25 mixture. Finally, the pellet is dried with acetone and evaporated in a centrifugal evaporator (RCT 60, Jouan, St Herblain, France). The residue is then taken up in 20 μl of H$_2$O/DMSO 85/15 solution and HPLC injection (conditions 1) is carried out in order to verify the absence of functionalizing reagent. 2 μl of nuclease P1 (ref.: N8630 Sigma-Aldrich, St Louis, USA) in solution at 1 U/μl in its buffer: sodium acetate 20 mM pH 5.5; ZnCl$_2$ 1 mM; NaCl 50 mM, and 1 μl of alkaline phosphatase at 7 u/μl in water (Ref. P7923-2KU Sigma-Aldrich, St Louis, USA) is added to the mixture. The mixture is left at room temperature for 4 to 6 hours. HPLC injection (conditions 1) is then carried out in order to verify complete hydrolysis of the ORN and to analyse the nature of the fragments.

The degree of functionalization is evaluated in UV at 260 nm, by integration of the multiplets corresponding to the acylated dinucleotides and to the acylated nucleosides, relative to the multiplets corresponding to the four ribonucleosides.

Note:

The values of the degree of functionalization presented in the context of this invention do not take account of the correction factor that must be applied as a function of the molar extinction coefficient at 260 nm of each of the nucleosides, whether they are nucleosides or dinucleotides.

FIG. 5 presents the results obtained in functionalization tests on 27-mer ORNs with the derivatives Biot-peg$_4$-SS-IAMe, as described in FR 1060102 and Biot-peg$_4$-SS-azaIAMe 14, at room temperature and at 65° C.

Discussion and Conclusion:

At 65° C., the uncorrected degree of functionalization was evaluated at 13.5% for the aza-isatoic derivative 14 against 7.5% for the reference compound, Biot-peg$_4$-SS-IAMe. The reactivity with respect to an oligoribonucleotide has therefore been increased by a factor of 1.8 in the aza-isatoic series at 65° C. More interestingly, the aza derivative 14 makes it possible to functionalize RNA at room temperature (uncorrected Df=7.8%), whereas the reference compound has very low reactivity in these conditions (uncorrected Df=1%).

With this example, we demonstrate the increase in reactivity with respect to an ORN with the aza-isatoic derivative 14, as well as its capacity for functionalizing an ORN at room temperature. It is also demonstrated that for one and the same concentration of reagent, an ORN is functionalized with the same Df at room temperature with the aza-isatoic derivative as at 65° C. with the isatoic derivative.

EXAMPLE 4: DEMONSTRATION OF THE CHEMO-SELECTIVITY OF RNA RELATIVE TO DNA IN THE AZA-ISATOIC SERIES

Objective:

In order to demonstrate the selectivity of functionalization of RNA versus DNA in the aza-isatoic series, a comparative test was carried out between an ODN with 27 bases and an ORN with 27 bases, reacted with an aza-isatoic derivative, Biot-peg$_4$-SS-azaIAMe (14).

Procedure:

8 nmol of ODN with 27 bases, Seq: 5'-AAC-CGC-AGT-GAC-ACC-CTC-ATC-ATT-ACA-3' (Eurogentec, Liege Science Park, Belgium) or 8 nmol of an ORN with 27 bases, Seq: 5'-AAC-CGC-AGU-GAC-ACC-CUC-AUC-AUU-ACA-3' (Eurogentec, Liege Science Park, Belgium) is reacted with the aza-isatoic anhydride derivative (14) at 30 mM in a mixture DMSO/buffer TEAAc (250 mM pH 7) 25/75, for 1 hour at room temperature. After precipitation with acetone and hydrolysis with nuclease P1 and alkaline phosphatase, the hydrolysed fragments are analysed by LC-MS, as described in example 3. An example of chromatograms for monitoring the reaction of the ODN or of the ORN with compound 14 is shown in FIG. 6, where traces A, B and C correspond respectively to the initial ORN, the ORN functionalized with compound 14 and precipitated, and the ORN functionalized with 14, precipitated and hydrolysed. Traces D, E and F represent the same results obtained with the ODN.

Results and Conclusion:

The uncorrected degree of functionalization of the ORN is evaluated at 7.8% with compound 14, whereas that of the ODN is evaluated at 0.5%. In these experimental conditions, the ODN is very little functionalized. These results confirm the selectivity of functionalization of the derivative of the aza-isatoic anhydride 14 for RNA and the absence of reactivity on the bases. In fact, if the bases reacted on compound 14, anthranilate nucleoside adducts resulting from a reaction with the ODN would be observed. Note that the 0.5% functionalization of the ODN is due to very low reactivity of the 5'-OH and 3'-OH ends of the DNA (see in this connection Nawrot Nucleosides and Nucleotides 1998 815-829).

This example demonstrates conservation of chemo-selectivity in the aza-isatoic series for an ORN relative to an ODN. The presence of 2'—OH groups specific to the ORN is the cause of the chemospecific reaction on the ORN.

EXAMPLE 5: SELECTIVE EXTRACTION OF HIV RNA TRANSCRIPTS FROM A SOLUTION CONTAINING A MIXTURE OF HIV RNA TRANSCRIPTS AND GENOMIC DNA

Objective:

The aim is to demonstrate that the concept of RNA enrichment of a biological solution, containing a mixture of RNA and DNA using the aza-isatoic derivative 14 as functionalizing reagent at room temperature is possible. For this, two biological models of nucleic acids were selected, HIV transcripts for RNA and genomic calf DNA. In order to compare the efficacy of the aza-isatoic derivative 14, these tests were also carried out on the reference compound Biot-peg$_4$-SS-IAMe at 65° C. and at room temperature.

Procedure:

The nucleic acids used in this example are as follows:

HIV transcripts WT 1500 bases, at 1.94 µg/µL.

gDNA calf thymus, SIGMA (Saint Louis, USA), ref. D4764-5UN, at 1.92 µg/µL.

1—Functionalization:

The following reagents are put in three 0.2-ml plastic tubes (Table 2 below):

TABLE 2

Synopsis of the experimental conditions described in example 5

| Tests | Mixture HIV transcripts/gDNA 1/9 at 2 µg/µL (in µL) | TEAAc 1M pH 7 (in µL) | Biot-peg$_4$-SS-IAMe at 6 mM/ DMSO (in µL) | Biot-peg$_4$-SS-azaIAMe at 6 mM/ DMSO (in µL) | Temperature |
|---|---|---|---|---|---|
| 1 | 6 | 3 | 3 | — | 65° C. |
| 2 | 6 | 3 | 3 | — | Rt |
| 3 | 6 | 3 | — | 3 | Rt |

In each case, the final concentrations of TEAAc and of functionalizing reagent are 250 mM and 1.5 mM respectively.

The three tubes are incubated for 1 hour at room temperature or at 65° C. on a heated rack.

2—Removal of the Surplus Functionalizing Reagent by Purification on Magnetic Silica:

Purification of the nucleic acids for each test was carried out in 5 different tubes of equivalent volume, in order to meet the optimum conditions for this step (i.e. 1 mg of magnetic silica per 2 µg of nucleic acids). Thus, each test is distributed in five 1.5-mL Eppendorf tubes i.e. 5 times 2.1 µL (2 µg of AN). 900 µL of lysis buffer (Easy Mag buffer, ref. 280134, bioMerieux, Marcy l'Etoile, France) and 50 µL of magnetic silica particles (EasyMAG silica, ref. 280133, bioMerieux, Marcy l'Etoile, France) are added to each tube. The latter are immediately stirred by the vortex effect after adding the silica, and then incubated for 10 minutes at room temperature. After magnetization on a DYNAL magnet, the supernatants are removed by aspiration with a pipette. For the next washing steps, the tubes are always stirred by the vortex effect and magnetized, followed by removal of the supernatant. A first washing is carried out with 500 µL of washing buffer 1 (Easy Mag buffer, ref. 280130, bioMerieux, Marcy l'Etoile, France). Two washings are then carried out with 900 µL and then 500 µL of washing buffer 2 (Easy Mag buffer, ref. 280131, bioMerieux, Marcy l'Etoile, France). Finally, a last washing step is carried out with 500 µL of elution buffer 3 (Easy Mag buffer, ref. 280132, bioMerieux, Marcy l'Etoile, France) at room temperature. Elution of the nucleic acids is carried out with 20 µL of elution buffer 3 stirred in a heated stirrer (1400 rpm) at 70° C. After 5 minutes, the tubes are stirred by the vortex effect and then magnetized to recover the supernatants. The latter are analysed with the Qubit® Fluorometer instrument, ref. Q32857, Invitrogen (Carlsbad, Calif., United States of America), and using the kits Quant-iT RNA Assay Kit 5-100 ng (ref. Q32855, Invitrogen, Carlsbad, Calif., United States of America), and Quant-iT dsDNA HS Assay Kit 0.2-100 ng (ref. Q32854, Invitrogen, Carlsbad, Calif., United States of America). These analysis kits allow an RNA/DNA ratio to be determined in a mixture.

3—Capture of Nucleic Acids on Streptavidin-Coated Magnetic Particles:

To perform this capture on magnetic particles, it is necessary to store each of the tests divided into 5 tubes in the preceding purification step. The optimum conditions for this step, i.e. the use of 40 µg of magnetic particles for completely capturing 2 µg of nucleic acids, are thus fulfilled. For each test, 8 µL (equivalent to 40 µg) of MagPrep P-25 Streptavidin, MERCK (Darmstadt, Germany) is put in five 0.2-ml plastic tubes beforehand. These particles are washed twice with 80 µL of PBS 1×+SDS 0.1%, using tapered tips and the MPC 9600 Dynal magnet Invitrogen (Carlsbad, Calif., United States of America) for the magnetic separations. Once the particles have been washed, 15 µL of nucleic acids purified in step 2 and then 5 µL of PBS 4×+SOS 0.4% are added to each pellet. The tubes are incubated for 10 minutes, stirring gently (vortex stirrer at minimum speed) at room temperature. After magnetic separation, the supernatants are recovered using tapered tips. This supernatant is analysed as before with the Qubit® Fluorometer.

4—Elution of the Functionalized RNAs:

The pellets of streptavidin magnetic particles, on which the functionalized nucleic acids are immobilized, are washed with 80 µL of PBS 1×+SDS 0.1% for 5 minutes at 65° C. (heated rack). The various tests are stirred by the vortex effect and after 5 minutes, the washing buffer is removed after magnetic separation using tapered tips. This operation is repeated twice. A last washing of the pellets is carried out with 20 µL of PBS 1×. The 5 pellets corresponding to each test are then mixed in a single tube. The volume is then 100 µL of PBS 1× for each test. These are stirred by the vortex effect, then the supernatant is removed after magnetic separation using tapered tips. Each pellet is suspended in 8 µL of a solution of DTT at 100 mM in PBS 1×. Each test is then stirred by the vortex effect, then incubated for 1 hour at 40° C., 300 rpm. After magnetic separation, the supernatant is recovered using tapered tips. This supernatant is analysed with the Qubit® Fluorometer instrument (Invitrogen, Carlsbad, Calif., United States of America) as before (about 100 ng of RNA is collected).

Results and Conclusions:

1—Results:

Analyses of the eluates with the Qubit® Fluorometer allow quantification of the nucleic acids present at each step of the process as described above.

From the measurements obtained, it is possible to calculate on the one hand the yields in extraction of RNA and of DNA, and on the other hand an intermediate selectivity index called S*. This index will enable us to compare several tests conducted with different isatoic derivatives:

$$S^* = \frac{Yld\ RNA\ \text{extraction}}{Yld\ DNA\ \text{extraction}} = \frac{[RNA]_{final} / [RNA]_{purifiedstep2}}{[DNA]_{final} / [DNA]_{purifiedstep2}}$$

Note:

Evaluation of the intermediate selectivity makes it unnecessary to take into account the bias that would be supplied by purification step No. 2. Based on the measurements obtained and the calculations that were carried out, the following Table 3 is established:

TABLE 3

Synopsis of the DNA/RNA ratios measured in steps 2 and 4 of the process for functionalization/capture/cleavage/elution of RNA

| | Tag at 1.5 mM | Temperature of functionalization | Initial DNA/RNA ratio | Final DNA/RNA ratio | S* |
|---|---|---|---|---|---|
| Test 1 | Biot-peg$_4$-SS-IAMe | 65° C. | 90/10 | 14/86 | 6 |
| Test 2 | Biot-peg$_4$-SS-IAMe | Rt | 90/10 | nd | nd |
| Test 3 | Biot-peg$_4$-SS-azaIAMe | Rt | 90/10 | 4/96 | 30 |

2—Conclusion:

The process of RNA enrichment, based on selective functionalization of RNA with the aza-isatoic derivative 14 at room temperature, is demonstrated. The DNA/RNA ratio thus changes from 90/10 at the end of the purification step, to a ratio of 4/96 after the complete process (test 3). This result demonstrates the efficacy of the aza-isatoic derivative 14 at room temperature for selective extraction of RNA.

Moreover, relative to the reference compound Biot-peg$_4$-SS-IAMe, this derivative makes it possible to enrich the mixture with RNA by performing the functionalization step at room temperature. Finally, the intermediate selectivity is increased by a factor of 5 at room temperature relative to the reference compound in the same conditions at 65° C.

The aza-isatoic derivative 14 allows ribonucleic acids to be functionalized at room temperature, with a consequent increase in selectivity of the extraction process with respect to RNA.

EXAMPLE 6: DEMONSTRATION OF THE CONCEPT OF THE SELF-IMMOLATING GROUP ASSOCIATED WITH A BIOTINYLATED AZA-ISATOIC ANHYDRIDE

Figure 1:
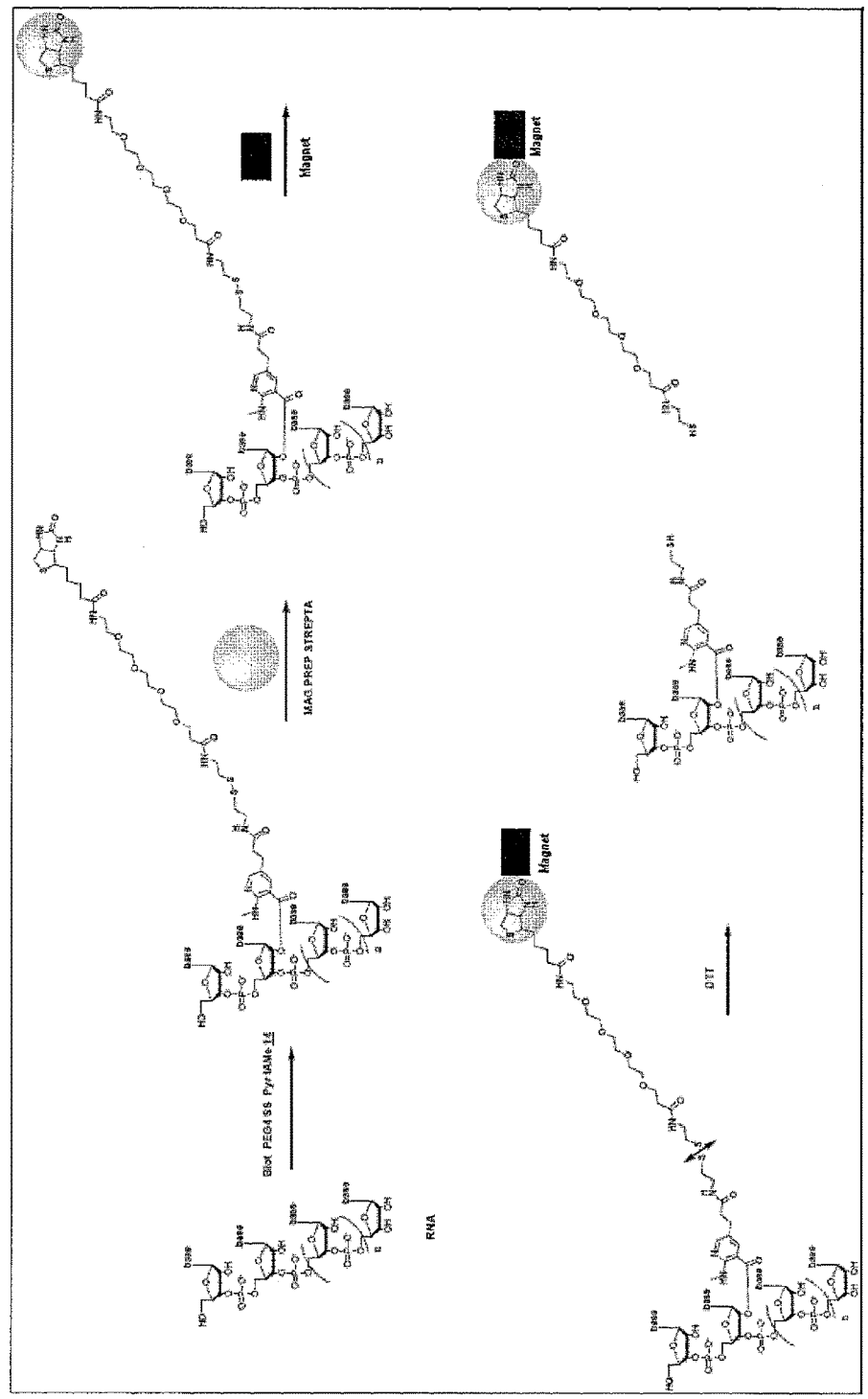
FIG. 1 shows the principle of RNA sorting using an aza-isatoic anhydride according to a first embodiment.
Figure 2:
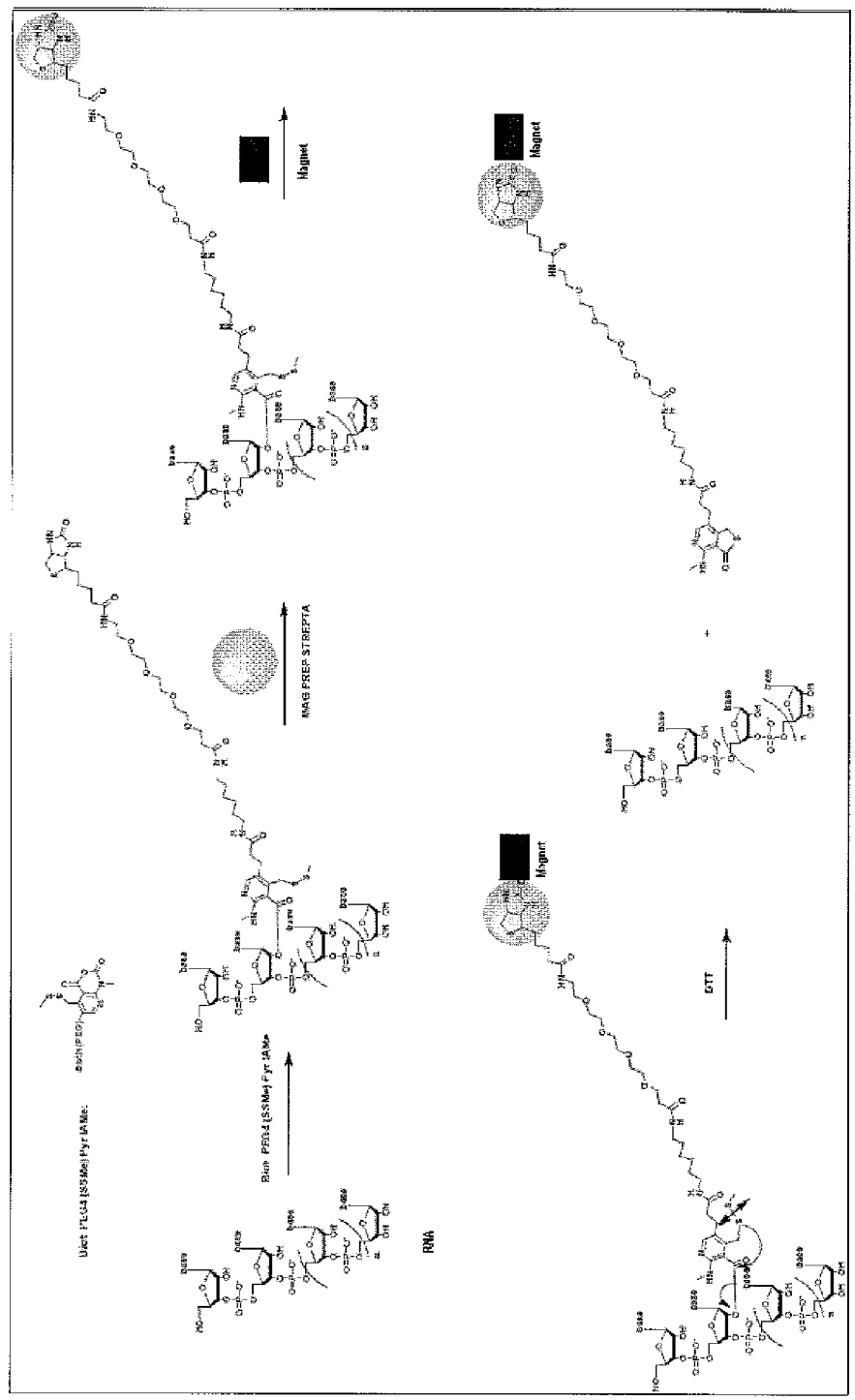
FIG. 2 shows the principle of RNA sorting in the presence of an aza-isatoic anhydride provided with a group inducing release of the molecule of "bare" RNA in a second embodiment, called self-immolating aza-isatoic anhydride.

Synthesis of an Aza-Isatoic Derivative Provided with a Disulphide Group on the Aromatic Moiety Synthesis of an aza-isatoic anhydride derivative, an example of which is described in FIG. 2, was carried out (BiotPE4(SSMe)PyrIAMe). It is provided with:
- a linkage having a dimethyl disulphide bond in the benzyl position and ortho to the carbonyl function
- a biotinylated derivative in the benzyl position.

After reaction of this derivative with a ribonucleic acid, the ribonucleic acid-aza-anthranilate conjugate that forms is treated with DDT, which hydrolyses the disulphide bond, and the thiol generated then reacts intramolecularly on the ester function of the aza-anthranilate by formation of a very stable aza-thiolactone. A bare ribonucleic acid free from aza-anthranilate is then liberated (FIG. 2).

The invention claimed is:

1. A functionalizing reagent of formula (I):

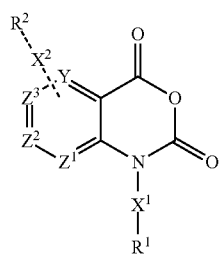

wherein:
Y represents $Z^4$ or the group $C—X^3—R^3$;
$R^1$, $R^2$ and $R^3$ represent, independently of one another, hydrogen (H) or a group of interest, where at least one of the radicals $R^1$, $R^2$ and $R^3$ represents the group of interest;
the group of interest is a marker, a labelling precursor, or a ligand;
$X^1$, $X^2$ and $X^3$ represent, independently of one another, a linkage;
only one of the radicals $Z^1$, $Z^2$, $Z^3$ and $Z^4$ represents nitrogen (N) when Y represents $Z^4$, and the other radicals each represent carbon with hydrogen (CH); and
only one of the radicals $Z^1$, $Z^2$ and $Z^3$ represents nitrogen (N) when Y represents the group $C—X^3—R^3$, and the other radicals each represent carbon with hydrogen (CH).

2. The functionalizing reagent according to claim 1, wherein Y represents $Z^4$ so that the functionalizing reagent has the following formula (1):

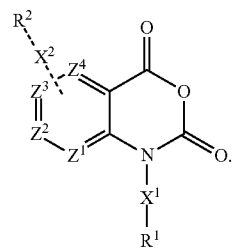

3. The functionalizing reagent according to claim 1, wherein Y represents the group $C—X^3—R^3$ so that the functionalizing reagent has the following formula (2):

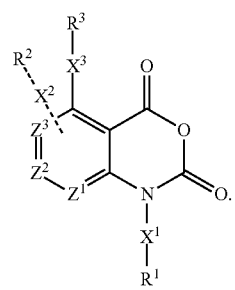

4. The functionalizing reagent according to claim 1, wherein the functionalizing reagent is immobilized on a solid support.

5. The functionalizing reagent according to claim 1, wherein each of the linkages $X^1$, $X^2$ and $X^3$ represents, independently of one another, a covalent bond or an optionally substituted carbon group having one or more carbon atoms and optionally containing an aromatic structure and/or heteroatom.

6. The functionalizing reagent according to claim 1, wherein one or more of the linkages $X^1$, $X^2$ and $X^3$ comprise a bond or function capable of being cleaved in a physicochemical, photochemical, thermal, enzymatic and/or chemical manner.

7. The functionalizing reagent according to claim 1, wherein the group of interest is the marker or labelling precursor.

8. The functionalizing reagent according to claim 1, wherein the group of interest is a marker having an intrinsic fluorescence.

9. The functionalizing reagent according to claim 1, wherein the group of interest is a marker not having an intrinsic fluorescence.

10. A functionalized RNA comprising RNA functionalized with the functionalizing reagent according to claim 1.

11. A kit comprising the functionalizing reagent according to claim 1.

12. A method of functionalizing RNA contained in a liquid sample, comprising:
reacting an anhydride function of the functionalizing reagent according to claim 1 with at least one hydroxyl group in any of (i) position 2' of riboses of nucleotides of RNA molecules, (ii) position 2' of riboses of nucleotides at terminal 3' ends of RNA molecules, or (iii) position 3' of riboses of nucleotides at terminal 3' ends of RNA molecules.

13. The method according to claim 12, wherein the group of interest has an intrinsic fluorescence.

14. The method according to claim 12, wherein the group of interest does not have an intrinsic fluorescence.

15. The method according to claim 12, wherein the group of interest is a ligand complementary to an anti-ligand and the method further comprises:
   capturing the functionalized RNA by binding the ligand with the anti-ligand.

16. The method according to claim 15, further comprising removing the captured RNA to obtain a DNA-enriched sample.

17. A method of separating RNA relative to other biological constituents including DNA, comprising:
   obtaining a functionalized RNA by performing the method according to claim 12 in a biological sample containing RNA and DNA wherein the group of interest is immobilized on a solid support that is able to be separated from the biological sample; and
   separating the functionalized RNA from the biological sample.

18. The method according to claim 12, wherein the anhydride function of the functionalizing reagent is reacted with the at least one hydroxyl group at room temperature.

19. The method according to claim 17, wherein the functionalized RNA is obtained by performing the method at room temperature.

* * * * *